US011065149B2

(12) United States Patent
Benyaminpour et al.

(10) Patent No.: US 11,065,149 B2
(45) Date of Patent: Jul. 20, 2021

(54) PORTABLE THERAPEUTIC SYSTEM USING HOT OR COLD TEMPERATURE

(71) Applicants: Behrouz Benyaminpour, Great Neck, NY (US); Jim Benjamin, Great Neck, NY (US); Ramin Benjamin, Grat Neck, NY (US)

(72) Inventors: Behrouz Benyaminpour, Great Neck, NY (US); Jim Benjamin, Great Neck, NY (US); Ramin Benjamin, Grat Neck, NY (US)

(*) Notice: Subject to any disclaimer, the term of this patent is extended or adjusted under 35 U.S.C. 154(b) by 650 days.

(21) Appl. No.: 15/515,769

(22) PCT Filed: Sep. 30, 2014

(86) PCT No.: PCT/US2014/058176
§ 371 (c)(1),
(2) Date: Mar. 30, 2017

(87) PCT Pub. No.: WO2016/053266
PCT Pub. Date: Apr. 7, 2016

(65) Prior Publication Data
US 2017/0246031 A1  Aug. 31, 2017

(51) Int. Cl.
*A61F 7/02* (2006.01)
*A61F 7/08* (2006.01)
(Continued)

(52) U.S. Cl.
CPC .............. *A61F 7/02* (2013.01); *A61F 7/0241* (2013.01); *A61F 7/086* (2013.01); *A61F 7/103* (2013.01);
(Continued)

(58) Field of Classification Search
CPC .......... A61F 7/02; A61F 7/0241; A61F 7/086; A61F 7/103; A61F 2007/0056;
(Continued)

(56) References Cited

U.S. PATENT DOCUMENTS 4,184,537 A  1/1980  Sauder
4,846,176 A  1/1989  Golden
(Continued)

FOREIGN PATENT DOCUMENTS

WO  WO 2005/112675 A1  12/2005
WO  WO 2008/129357 A2  10/2008
(Continued)

OTHER PUBLICATIONS

International Preliminary Report on Patentability (IPRP) in PCT/US2014/058176.
(Continued)

*Primary Examiner* — Kaitlyn E Smith
(74) *Attorney, Agent, or Firm* — Ted Whitlock

(57) ABSTRACT

Disclosed is a system which employs a cooling or heating pad which is preferably rechargeable with hot or cold temperatures at an intended area of the body. The pad includes a highly temperature-conductive or temperature-retentive material which can be cooled or heated using a portable source of heat or cold material delivered to the pad by a removable delivery conduit. Valves can be included to regulate flow of the cooling or heating material from the source to the pad. The system can also include a dual-chambered canister for containing two different media for heating, cooling or for alternating heating and cooling the pad.

8 Claims, 13 Drawing Sheets

(51) Int. Cl.
*A61F 7/10* (2006.01)
*A61F 7/00* (2006.01)

(52) U.S. Cl.
CPC ............. *A61F 2007/0054* (2013.01); *A61F 2007/0056* (2013.01); *A61F 2007/025* (2013.01); *A61F 2007/0225* (2013.01); *A61F 2007/0244* (2013.01); *A61F 2007/0246* (2013.01); *A61F 2007/0247* (2013.01); *A61F 2007/0252* (2013.01); *A61F 2007/0273* (2013.01)

(58) Field of Classification Search
CPC ...... A61F 2007/0244; A61F 2007/0246; A61F 2007/0247; A61F 2007/025; A61F 2007/0252; A47C 27/081; B60R 21/231; B60R 21/232; B60R 21/235; B60R 2021/23316; B60R 2021/23509; B60R 2021/23514; B60R 2021/23538; B60R 2021/23561; B60R 2021/23576; B60R 2021/23595; D05B 1/26; D06B 1/10
See application file for complete search history.

(56) References Cited

U.S. PATENT DOCUMENTS

| | | | |
|---|---|---|---|
| 5,737,774 A * | 4/1998 | Petty-Saphon | A61F 7/02 2/44 |
| 6,375,674 B1 | 4/2002 | Carson | |
| 8,052,628 B1 | 11/2011 | Edelman | |
| 8,491,644 B1 | 7/2013 | Carson | |
| 9,149,386 B2 * | 10/2015 | Fahey | A61N 1/0452 |
| 2001/0018605 A1 | 4/2001 | Helming | |
| 2006/0142828 A1 * | 6/2006 | Schorr | A61F 7/034 607/108 |
| 2009/0235680 A1 * | 9/2009 | Serrano Molina | A41D 13/0053 62/259.3 |
| 2009/0312823 A1 * | 12/2009 | Patience | A61F 7/007 607/104 |
| 2010/0100090 A1 | 4/2010 | Rose | |

FOREIGN PATENT DOCUMENTS

WO  WO 2009/056296 A1  5/2009
WO  WO 2014/055082 A2  4/2014

OTHER PUBLICATIONS

International Search Report (ISR) and Written Opinion (WO) in PCT/US2014/058176.

\* cited by examiner

PORTABLE THERAPEUTIC SYSTEM USING HOT OR COLD TEMPERATURE

BACKGROUND OF THE INVENTION

Cooling or heating pads are well known in the art and have been used for therapeutic procedures for many years. Currently available cooling or heating pads typically require prior refrigeration/cooling/freezing or heating/warming of the pad, as the case may be, by placement of the pad within an external heat or cold source. In order to provide continuous therapy, these prior cooling or heating pads may require more than one pad so that a "reserve" pad can be refrigerated/frozen ("cooled") or heated while another is in use. In addition, such pads typically use bulky materials which prohibit free mobility of injured treatment area of the body and can be uncomfortable to wear during normal activities.

Cooling or heating pads in the prior art generally employ a gel or similar temperature-retentive material to maintain cold or hot temperatures generated by the external-cold or heat source, whereby the cooled or heated pad is placed within the source of cold or heat (e.g., refrigerator/freezer for cold; boiling water or oven, such as a microwave oven, for heat) and is then removed from the cold or heat source so that it can be applied to an intended area of the body in need of treatment using cold or hot temperatures. Moreover, when re-cooling or re-heating of the pad is required, the pad must be removed from the treatment area and replaced with another pad, such as a reserve pad or the same pad after re-cooled or re-heated.

A common method of alleviating pain or swelling after a surgical procedure or accidental injuries is to use a cold compress, using an ice bag, a bag of frozen peas, or snow-type freezer packs to be wrapped around or applied to the affected area. Currently available cooling pads require pre-cooling or pre-freezing of the pad whereby the pad is physically placed within the cold source (refrigerator, freezer, ice-filled container, or the like) prior to use. Similarly, heating pads are pre-heated prior to use. Heat therapy, using a heating pad warmed by an outside source (e.g., heated or boiled water, microwave oven, or the like) or filled with a heated liquid, such as hot or boiling water, can be used as an alternative to, or in combination with, cold therapy to relieve pain or soreness in an area of the body.

It would be understood that any discussion of the prior art, and the disadvantages thereof, in the context of cool or cold packs and therapy would apply equally but in some cases, oppositely, to heat or hot-packs and therapy. Similarly, any discussion of the prior art, and the disadvantages thereof, in the context of heat or hot-packs and therapy would apply equally but oppositely to cool or cold packs and therapy.

Certain cooling devices utilize cold liquid to circulate around the affected area and require tubes carrying the liquid to be continuously connected to the device whereby use of the device is inconvenient and bulky. Moreover, bulky cooling pads or cold packs are limited as to their applicability to certain parts of the body. For example, specific areas of the face, such as the brow or nose, generally require the pad or pack to cover the whole, general area and cannot provide a truly moldable device which substantially conforms to areas of the body which are not easily enwrapped.

A pad which is pre-cooled or frozen generally adapts its shape to the environment of the cold source. For example, even a flexible ice pack, when frozen, is generally defined by the shape of its outer container. When placed in a freezer, ice packs are typically formed in a generally rectangular shape with generally flat faces for contacting the body. Although they can be frozen in a particular or pre-formed "curved" shape, it is well recognized that the curvature only generally mimics the shape of the body at the site of application and does not mold to the specific contours as would be desired.

The previously available processes, though effective, are inconvenient and can limit mobility of the person due to the weight or bulkiness of the ice or cooling pack. None of the previous devices known to the inventors can provide cold therapy "on demand" without requiring removal of the pad to replace cold or hot temperatures, and without the use of bulky materials or requiring continuous circulation of liquid through the device during use.

Thus, what is needed is a cooling or heating pad device and system that can efficiently provide cold or heat to a specific area of the body. Preferably, this desired action is achieved by a system comprising a pad that can be "charged" with cold or heat at the time of use and at the site of use so that the pack does not require extended periods of time to cool down or become frozen, or to warm up to a desirable temperature before use. Neither would such system require removal of the pad for re-cooling, re-freezing, or re-heating following dissipation of the therapeutically effective cold or hot temperature after a period of time.

Moreover, what is needed is a system which can provide a "re-chargeable" pad which can be re-cooled or re-heated during use that may not require continuous connection or link the external source. Thus, a pad and system providing an external source of cold or heat which is connected to the pad temporarily, only to provide cold or heat to the pad, and then may be is disconnected from the pad during use, advantageously provides greater mobility and ease of use to and for the user of such pad and system.

Preferably, the cooling or heating pad is flexible or malleable or moldable to conform to the shape of the body area in need of treatment or being treated.

These advantages, as described herein, as well as other advantages that would be recognized and appreciated from this disclosure, are achieved by the subject invention which overcomes the disadvantages and inconvenience of cold and heat packs known or currently available in the art.

SUMMARY OF THE INVENTION

The subject invention provides a system and method for cooling or heating an area of the body which is advantageously safe, convenient, portable, and is compact in that it does not require the use of bulky materials. The system and method preferably comprise a thin, flexible pad or "wrap" comprising a highly efficient temperature-retentive material which can be activated using a cooling or heating medium to provide cold therapy or heat therapy on-demand, as well as being capable of being reactivated or "recharged" on-demand.

The system and method of the invention further comprise a portable source of endothermic (cooling) or exothermic (heating) medium to cool or heat the pad. The heating or cooling medium can be delivered to the pad via a conduit, such as a connecting rod or tube, which has a connecting means at one end compatible with and engaging or adjoining to the source of the heating or cooling medium, and a second connecting means at its other end compatible with and adjoining to the pad to deliver the cooling or heating medium to the temperature-retentive material within the pad.

In summary, the invention comprises a portable heating or cooling pad system for rechargeably applying hot or cold temperature therapy to an area of a body in need of such treatment using hot or cold temperature, the system comprising:
- a pad comprising a layer of highly efficient temperature-retentive material;
- a detachable delivery conduit for delivering the heating or cooling medium from a source to the temperature-retentive material; and
- a portable source of cooling or heating medium within a container, said medium being deliverable to the temperature-retentive material by the removable delivery conduit, as desired, to cool or heat the temperature-retentive material, and thereby the pad, for use.

Preferably, the pad is lightweight, comprising lightweight materials. Preferably, the pad is flexible, malleable, or moldable, comprising flexible, malleable, or moldable materials.

The temperature-retentive material and pad can be cooled or heated at the site of use without requiring removal of the pad or without requiring continuous circulation of the medium from the source to the pad during use. Accordingly, the pad can be activated and recharged at the site of use without removing or replacing the pad.

The system can further comprise a connecting conduit engaged or integral with the pad or the source of the cooling or heating medium. The connecting conduit can be a hollow tube or a solid rod. Preferably, the connecting conduit further comprises a delivery port for delivering cooling or heating medium from the source to the pad or temperature-retentive material therewithin.

The source of cooling or heating medium is preferably a canister capable of holding the cooling or heating medium under pressure, and preferably comprises a nozzle in communication with a chamber within the canister, allowing delivery of the medium from the chamber to the conductive material. The nozzle preferably comprises a valve for regulating flow of pressurized cooling or heating medium from the canister.

The heating or cooling medium is a medium providing exothermic or endothermic conditions to the conductive layer or material of the pad, and is typically a cooling medium such as liquid nitrogen, Freon gas, refrigerant gas r-134a, or the like.

The system employs a heating or cooling pad for applying hot or cold temperature to an area of a body in need of treatment using hot or cold temperature. Preferably, the pad comprises a thin, flexible layer of highly efficient temperature-retentive material heated or cooled by an external heating or cooling medium deliverable to the temperature-retentive material while the pad is in use on the body. The heating or cooling medium can be delivered to the temperature-retentive material or layer by way of a connecting conduit engaged with or connected to the temperature-retentive material or a chamber in communication with the temperature-retentive material.

The connecting conduit can further comprise a delivery port for receiving the heating or cooling medium, whereby the delivery port is engaged or integral with, or connected or affixed to, the connecting conduit.

The heating or cooling pad can further comprise one or more protective layers or protective covers surrounding the temperature-retentive material. The outer surface of the covering material can comprise any material typically used for protection when applied next to the skin of a user, and can be present for purposes of protecting the conductive material from perspiration, oil, or compositions, such as skin lotions, applied to the skin.

Alternatively, the pad can comprise an outer cover on one face of the conductive material. For example, an outer cover can be formed over an inner face of the pad contacting the skin of the user, said outer cover being useful for conducive to temperature transfer from the temperature-retentive material to the body area in need of therapy. The covering over the inner face can comprise a material which allows heat or cold transfer from the conductive material to a surface of the cover. Preferably, such cover material is a polymeric or textile material.

Alternatively, an outer cover can be provided on an outer face of the pad, the outer face being opposite a face of the pad contacting the skin when in use, said outer covering being useful for or conducive to insulating the temperature transfer from the temperature-retentive material. The covering over the outer face of the conductive material preferably comprises an insulating material for retaining or directing the heat or cold to toward the skin of the user. The insulating material can be a porous or non-porous polymeric material having temperature insulating properties. Porous material can be the result of pores formed naturally in the manufacture of the material or can be formed by physical formation of pores in a non-porous material. For example, micro-pores can be formed in a non-porous material using a laser drill.

Preferably, the heating or cooling pad comprises a temperature-retentive material, such as graphene, aluminum oxide, or the like, or a composition comprising the temperature-retentive material, e.g., a gel material, liquid, or fabric comprising graphene, aluminum oxide, or the like. These temperature-retentive materials can be provided as solid "plates" or sheets, powder, beads, or "fibers." When the conductive material is a powder or beads, it is preferred that the material is contained within a thin bladder forming the pad. The conductive material can be used alone or in combination with a gel composition, as known in the art for use with heating or cooling pads. Alternatively, the temperature-retentive material can be one or more layers of readily available textile or fabric comprising highly conductive microwire filaments or alloys that allow retention and transfer of the cold or hot temperature to the skin. The layers may be fused together and may be covered with layer of gel or highly conductive layer of (insulating) thermal pads as is currently used in electronic industry to transfer heat.

A preferred embodiment comprises a temperature-retentive material which is encased or enwrapped within a thin layer or membrane to form a unitary temperature-retentive packet. The layer or membrane can comprise one or more plastic or polymeric material, metal foil, or a combination of these materials provided in separate or fused layers. In addition to temperature transfer or insulating properties that can be provided by the outer covering of the temperature-retentive packet, the outer covering of the temperature-retentive packet can also advantageously be removed and replaced if damaged, aged, or is otherwise sub-optimally functional.

The temperature-retentive packet can be formed having a flange or flanged edging as part of the outer covering, whereby the temperature-retentive packet can be secured in place by affixing the flange or flanged edging to an outer housing or covering of the pad. For example, the outer pad housing can comprise a holding peg or "snap" means onto which the flange or flanged edging can be removably affixed. Alternatively, the housing can be formed to comprise a ridge or rib onto which a retaining ring (e.g., an O-ring) can be affixed over the flange or flanged edging of the temperature-retentive packet.

Preferably, the temperature-retentive packet can be disposable, and can be removed and replaced as desired by the user. For example, the system can comprise one or more cold-retaining temperature-retentive packet, one or more heat-retaining temperature-retentive packet (if requiring a different temperature-retaining material), or one or more of both. In this way, the user can provide cold therapy or heat therapy on-demand by using one temperature-retaining packet, removing it when therapy is complete, and replacing it with another temperature-retaining packet.

One preferred embodiment of a cooling pad according to the invention comprises a single chamber within the pad wherein an outer housing or cover encloses the chamber which can receive and retain a cooling medium, or coolant, such as liquid nitrogen, Freon gas, refrigerant gas r-134a, or the like. The outer housing can be formed or molded as a single unit, or can be provided as one or more adjoining units which are fitted together to form the outer housing of the pad.

In another embodiment, the pad can comprise a plurality of chambers. For example, the pad can comprise two chambers—a lower chamber and an upper chamber. These lower and upper chambers can be a single divided chamber or can be separately formed chambers divided from one another by a wall or layer therebetween, forming two or more discrete chambers. The upper chamber or chamber portion is generally hollow, and comprises a port for delivering the coolant to the chamber. The lower chamber portion or lower chamber can comprise a gel or other coolant-retaining substance which receives coolant from the upper chamber or portion and which can retain cold temperature for an extended period of time up to about two hours before recharging with coolant. Typical use of cold or heat pad is on average 15 to 20 minutes for therapy purposes. It is possible that one can connect the tube conspicuously at all time and the nozzle will intermittently inject the freezing gas in an automated fashion which then frees the individual from needing to recharge directly. The maximum time the disposable ica packs is claimed to cool in 30 minutes, and in reality it is cold for no more than 15 minutes (versus controlled environment as it claimed).

In one preferred embodiment, the outer housing can be flexible, having elastic or expandable properties, allowing for expansion of the one or more chambers so that the volume of the one or more chambers can increase for receiving an excess amount of coolant when charging the cooling pad. Ports or vents can be provided to allow excess coolant to escape from the chamber following charging of the temperature-retaining material disposed within the chamber. For example, in one embodiment, the outer housing comprises a readily-available material, such as Santoprene® (Monsanto, St. Louis, Mo. USA) which has a desired porosity and allowing the cooling or heating medium to escape from the chamber. Flexibility of materials forming the outer housing can also facilitate contouring of the cooling pad device to a particular shape of a body area. In other words, the outer housing can be rigid and molded to a particular shape, or can be semi-rigid to flexible to be conformed to shape of the area of the body where therapy is needed.

In use, the pad comprising the one or more chambers is positioned next to the body part in need of cold or heat therapy. Preferably, one or more chambers does not directly contact the body, but is separated from the body or skin by the flexible housing or outer covering surrounding the one or more chambers. The flexible housing or outer covering of the cooling pad can comprise a temperature conducting material in the area contacting the skin so that the effect of the charged chamber passes to the skin and body part when in contact with the pad.

In one embodiment of two-(or more) chambered pad, the upper and lower chamber or chambers can be divided from one another by a porous wall or layer wherein the pores provide for transfer of coolant from the upper chamber (which received the cooling or heating medium) to the lower chamber and the temperature-retaining material therein. Preferably, the porous wall or layer is flexible so that it can conform to the desired shape of the body area when in position for use. In addition, the pores can be formed inherently by a woven textile material, or can be holes or apertures formed in a solid sheet of non-porous material.

In one embodiment, the pores, holes or apertures are formed having sizes which are graduated, e.g., smaller holes or apertures at one end which are increasingly larger toward the other end. For the subject invention comprising graduated sizes of the pores, the smaller-sized holes are preferably formed at the end of the pad where the delivery port is located and the larger pores are formed at the end away from the delivery port. In this graduated pore size configuration, less coolant is immediately transferred to the lower chamber at the delivery port end since the smaller pores resist transfer of the coolant. The larger pores at the distal end away from the delivery port provide more rapid transfer of coolant to the lower chamber. Accordingly, the graduated pore size configuration has been found to provide a more even or consistent delivery of coolant to the entire lower chamber.

It is further noted that an insulating layer can be provided between the one or more chambers or chamber portions and the outer flexible housing. Preferably, this insulating layer is provided between the upper portion of the upper chamber or chamber portion and the outer flexible housing to reduce or slow down temperature equilibration between the cooling pad and the exterior environment. It is preferred that an insulating material is not provided between the lower chamber or chamber portion and the inner face of the outer flexible housing which contacts the body because transfer of cold temperature from the lower chamber to the body is desired and presence of an insulating material between the lower chamber and the body can prevent or reduce such desired transfer of temperature.

It is understood that the cooling pad described above can be adapted for heat therapy by substituting a heat-providing or exothermic substance in place of coolant. For example, steam or heated water or an exothermic gas or liquid can be delivered to the chamber so that the temperature-retentive material and the pad is heated and transfers heat to the body area when positioned next to the body.

For securing the pad in position in relation to the area of the body in need of treatment, the pad can further comprise an attachment means. The attachment means can be affixed to the pad or a cover of the pad. As recognized in the art, the attachment means can be any suitable and available strap, or the like, and can comprise a buckle, snap, or hook and loop material for affixing the attachment means in place on the body when in use.

A further embodiment of the invention comprises a canister for containing two media for heating or cooling. The canister comprises an outer housing wall bounding a two chambers within the canister, said two chambers formed by a longitudinally oriented dividing wall within the canister and defining first and second chambers. The first and second chambers independently contain a first and second medium wherein said first and second media are selected from (a) an endothermically reacting media forming a cooling medium when mixed together,
(b) an exothermically reacting media forming a heating medium when mixed together, or
(c) a cooling medium in the first chamber and a heating medium in the second chamber.

The canister can comprise first and second nozzles, wherein the first nozzle communicates from outside the canister to inside the first chamber, and the second nozzle communicates from outside the canister to the second chamber. The canister can further comprise a valve for regulating flow of cooling or heating media from within a chamber of the canister.

Use of the system of the invention provides an advantageous method of providing heat or cold therapy to an area of a body. Specifically, the method of the invention comprises the steps of:
(a) providing a pad comprising a layer of highly efficient temperature-retentive material;
(b) applying the pad to the area of the body in need of heat or cold therapy; and
(c) cooling or heating the temperature-retentive material using a cooling or heating medium from an external source to cool or heat the temperature-conductive material and thereby cool or heat the pad.

A preferred method can further comprise recharging the temperature-retentive material on-demand, without removing the pad from its position on the body.

A preferred method is carried out whereby the conductive material is cooled using liquid nitrogen or other liquid or gas cooling medium. Alternatively, the method can advantageously employ alternating heat and cold therapy using the pad without removing the pad between heat and cold therapies.

The subject invention can advantageously be used at very specific areas of the body. Preferred embodiments of the subject invention provide a cooling or heating surface which can be contoured or molded to curvatures of the affected area such as such as a knee, ankle, shoulder, or smaller area such as the bones around the eye or nose, or any other part of the body as needed.

Due to the portability of the pad and cooling or heating medium, an individual using the system or carrying out a therapeutic method using the system can advantageously continue all normal activities while wearing the pad, and can re-cool or re-heat the pad without removing the pad when the heat or cold dissipates.

The heating or cooling medium can advantageously be delivered to the temperature-retentive material as desired, or as needed, ("on demand"), by a user, for example, by a connecting means which is in removable communication with a source of heat or cold medium.

The method comprises providing a pad, as described above, contacting a temperature-retentive material of the pad with a heating or cooling medium such that the outer surface of the pad becomes cold or hot as intended. The pad is applied to the outer surface of the skin at an area of the body in need of such hot or cold treatment. The heating or cooling medium can be delivered to the temperature-retentive material of the pad by a tube or conduit in communication therewith. For example, for delivering a cooling medium to the temperature-retentive material, a stand-alone or portable canister of liquid nitrogen or other liquid, refrigerant gas r-134a gas or alike (e.g., Freon) or solid (preferably, fluid) can be used, which delivers cooling or heating medium to the temperature-retentive material via a conduit (e.g., a flexible tube) which is in communication with the pad, or in direct communication with the temperature-retentive material.

The conduit or tubing can have an engagement means for affixing it to a port provided in the outer housing of the pad, or the conduit or tubing can pass through the wall of, and extend within, the housing, and comprise one or more ports in the tubing or branches of the tubing which deliver and disperse cooling or heating medium across a wide surface area of the temperature-retentive material.

More preferably, the canister or communicating tube or conduit comprises a valve for regulating the flow of medium to the conductive layer, including a shut-off position to completely stop the flow of medium to the temperature-retentive material.

The subject system and method is ideal for use when traveling, at home or at office and provides instant cold/heat therapy when needed and have numerous applications, including for post-surgical treatment of an area of the body, reduction of fever or hyper- or hypothermia conditions, for minimizing bruising, for emergency application in minimizing tissue damage following a heart attack, for fertility purposes (such as maintaining coolness in the groin or scrotal area).

A preferred device can be shaped to conform to a particular area of the body, and can be gender-specific, such as for women following breast augmentation procedures, or for men following vasectomy or hernia repair procedure. The malleability or molding capability of the pad to conform to a specific area of the body is facilitated by the portability of the pad. Specifically, the pad can be placed at the site to contact the body in a form-fitting manner, then frozen in situ using the cold or heat medium. This is advantageous over conventional freezer packs which are only generally contoured to fit the specific area of the body by being frozen in a freezer, then removed to be placed onto the area of the body.

In addition, the subject invention contemplates incorporating the pad into or as part of clothing, including underwear or outer apparel. Outer apparel can include sports uniforms or protective gear, or military uniforms.

Another advantage of the subject invention is that the temperature-retentive material of the pad can receive either one of a heating or cooling medium, such that the therapies can be interchanged, for example, alternating heat or cold for using both therapies on the same area of the body, without changing or replacing the pad between therapies. Some treatments require cold therapy to reduce inflammation and after certain amount of time to administer heat therapy to expand the blood circulation and flow of blood and dispose of lactic acids to help healing of the injured muscles.

As a further aspect of the invention, a dual-chambered canister can be used as a source of heating or cooling medium for the desired treatment or for alternating heat and cold treatments. One embodiment of the invention includes a dual-chambered canister having a first chamber containing a cold-temperature or cooling medium, and a second chamber containing a hot-temperature or heating medium.

It is therefore an object of the subject invention to provide a convenient and portable means of cold (or heat) therapy which overcomes certain disadvantages of the currently available cooling or heating pads. Advantageously, a device in accordance with the subject invention is lightweight, substantially compact, and portable.

It is a further object of the invention to provide a pad and method for heat or cold therapy which does not require a continuous circulation of cold or hot liquid or fluid through the pad during its use on or around a body part.

The design and contour of the pad comprises a relatively thin, flexible material which can allow the device to be molded to closely contour the shape or curvature of the treated area of the body, allowing the person to wear normal clothing and perform normal activities while the cool or hot therapy pad is in use. Further, the subject device and method do not require removal and replacement of the pad when further cooling or heating is desired.

BRIEF DESCRIPTION OF THE DRAWINGS

FIG. 10 shows views A-G, illustrating various views of one embodiment of the invention.

DETAILED DESCRIPTION OF THE INVENTION

Figure 1:
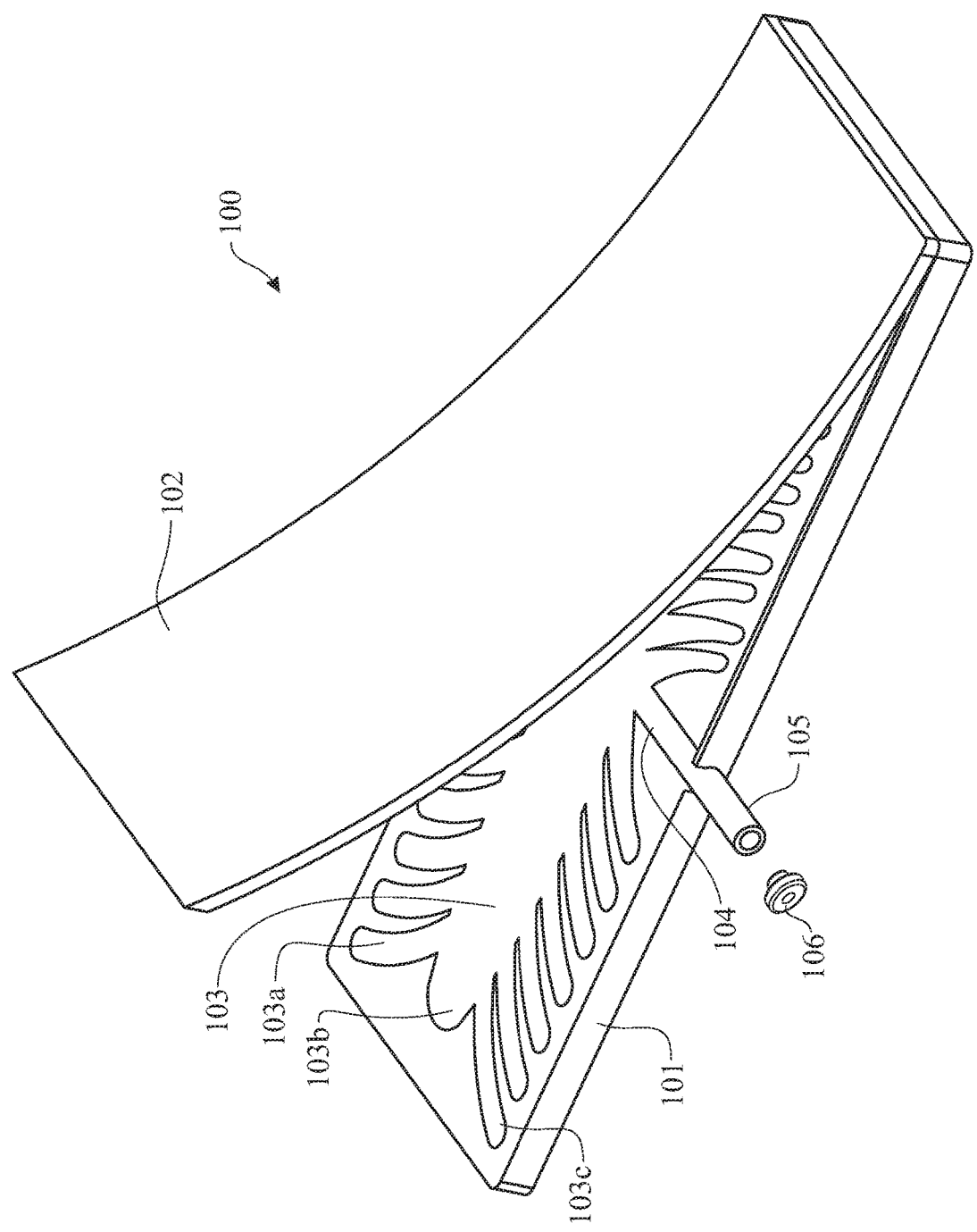
FIG. 1 shows a partially exploded perspective view of an embodiment of a pad of the invention, illustrating the temperature-retentive material, the outer covering, and charging conduit, including a charging port.

The subject invention provides a system and method for cooling or heating an area of the body using a flexible pad or "wrap" which can be activated or charged with a cooling or heating medium on demand to provide cold therapy or heat therapy at a site or area of the body in need of heat or cold therapy. The system and method of the subject invention is advantageously safe, convenient, portable, comfortable, and is compact in that it does not require the use of bulky materials.

The system of the subject invention comprises a heating or cooling pad device comprising a temperature-retentive material disposed within one or more chambers defined by an outer housing or cover which can be rigid, semi-rigid, or flexible when in use. The pad can advantageously be used at very specific areas of the body. A preferred embodiment of a pad of the subject invention has minimal thickness and high flexibility such that the pad can be contoured or molded to curvatures or contours of a target area of the body, such as a knee, ankle, shoulder, or areas such as the bones around the eye or nose, or any other part of the body as needed.

Due to the portability of the system, the individual using the system or employing a therapeutic method using the system can continue all normal activities while wearing the device.

The subject invention employs a cryo- or heat-therapy system or method employing a pad which comprises a highly efficient temperature-retaining or temperature-conducting material which can be activated or "charged" by contacting the temperature-retaining material with a cooling or heating medium. Advantageously, the cooling or heating medium can be used to activate or charge the temperature-retentive material while the pad is in place on the body, and can be re-activated or re-charged without removing the pad from the body.

The temperature-retentive material is preferably provided as a relatively thin layer, bounded or covered by a polymeric material or textile which allows the cold or hot temperature to be carried from the temperature-retentive material to an outer surface of the pad, thereby cooling or heating the surface of the skin when contacted by the cold or heat activated or charged pad. The heating or cooling medium can advantageously be delivered to the temperature-retentive material as desired by a user, for example, by a connecting means which is in removable communication with an external source of heat or cold medium.

For purposes of the subject invention, cooling or heating of the temperature-retentive material or the pad comprising the temperature-retentive material, can be referred to as "charging" the temperature-retentive material or pad. Thus, re-cooling or re-heating of the temperature-retentive material or pad comprising the temperature-retentive material is referred to as "re-charging" the temperature-retentive material or pad comprising the temperature-retentive material.

The subject method comprises providing a pad comprising a temperature-retentive material described above, contacting the temperature-retentive material with the heating or cooling medium such that the pad is "charged" with heat or cold temperature, and the outer surface of the pad becomes cold or hot as intended. The pad can then be applied to the outer surface of the skin at an area of the body in need of such hot or cold treatment.

The heating or cooling medium can be delivered to the temperature-retentive material by a tube or conduit in communication with therewith. For example, for delivering a cooling medium or coolant to the temperature-retentive material, a stand-alone or portable canister of liquid nitrogen or other cooling gas, liquid, liquefied gas, or solid capable of being contained in a portable canister, can be used. Preferably, the canister or communicating tube or conduit comprises a valve for regulating the flow of cooling or heating medium to the temperature-retentive material, including a shut-off position to completely stop the flow of cooling or heating medium to the temperature-retentive material.

The subject system and its components can be readily understood by reference to the drawings attached hereto. FIG. 1 shows the cooling or heating pad 100 comprising two substrate layers 101 and 102 made from a flexible material and forming an outer cover for the pad. The flexible substrate materials can be a polymeric material or textile, and are preferably a material which is non-irritating or hypoallergenic to skin. The substrate layers can be the same or different. In one preferred embodiment, the substrate layers comprise a first substrate layer which is intended to contact the skin (the inner layer) and a second substrate layer forming the outer surface (non-skin-contacting, or outer, layer).

The substrate layer contacting the skin is preferably non-insulating or comprises a non-insulating or temperature-conductive layer, whereby the heat or cold is readily transferred from the pad to the skin and surrounding area. The outer layer is preferably insulating or comprises a temperature-insulating layer, whereby the cold or heat is prevented from dissipating from the pad to the outer environment, thereby retaining the heat or cold temperature within the pad, or actually serving to direct the heat or cold toward the skin surface.

In one preferred embodiment, the outer substrate can comprise pores, preferably micro-pores, that can allow gas and/or air pressure be relieved from the pad. Micro-pores can be formed in a substantially non-porous material by means of a laser drill. One advantage of a microporous outer substrate is the capability to relieve pressure without a valve.

Layered proximate to or between the substrate materials 101 and 102 forming a pad cover, is a highly efficient temperature-retentive material 103. The temperature-retentive material is preferably thin layer(s) of a metal, carbon, or ceramic, such as graphene, aluminum oxide, or the like, or a material having temperature-retentive or temperature-conductive properties similar to these materials. It would be understood that the temperature-retentive material can be a composition comprising the temperature-retentive material, e.g., a gel material. or can be a conductive fabric that may compromise highly conductive fiber alloys, not excluding graphene, aluminum oxide, or the like.

These temperature-retentive materials can be provided as solid "plates" or sheets, powder, beads, or as "fibers" or microwires formed as, or in, a fabric. When the conductive material is a powder or beads, it is preferred that the material is contained within a bladder forming the pad. The conductive material can be used alone or in combination with a gel composition, as known in the art for use with heating or cooling pads. Alternatively, the temperature-retentive material can be one or more layers of readily available textile or fabric comprising highly conductive microwire filaments or alloys that allow retention and transfer of the cold or hot temperature to the skin. The layers may be fused together and may be covered with one or more layers of gel or highly conductive layer of insulating material as is currently used in electronic industry to transfer heat.

Alternatively, the temperature-retentive material can be provided within a thin bladder containing within the bladder a highly temperature-conductive material such as aluminum oxide. Aluminum oxide can be provided as a powder, or as small beads. Other temperature-conductive or temperature-retentive materials, such as a polymeric gel, in the form of beads, or as a fluid, can also be included within the bladder, with or without aluminum oxide.

The temperature-retentive material is shown in FIG. 1 as having radiating extensions or "arms" 103a, 103b, and 103c, extending from a central core 103, to provide or distribute cold or heat to all areas of the pad within the cover. It would be understood that the conductive layer can be any shape, including rectangular, oval, circular, or amorphous, such that the heat or cold is provided to all areas of the pad, and preferably equally distributed to all areas of the pad.

In order to provide cold or heat to the temperature-retentive material, the temperature-retentive material is configured so that it can be in communication with an outside source of cold or heat, preferably an endothermic or exothermic medium serving as the cold or heat source, respectively. Cooling media useful in connection with the subject invention include, but are not limited to, inert gases (in gaseous, liquid or solid form) such as liquid nitrogen, argon, carbon dioxide (dry ice), chlorofluorocarbons, e.g., Freon, fluorocarbons such as pentafluoropropane, tetrafluoroethane, refrigerant gas r-134a, or the like, or conventional ice or gel. Heating media include any exothermic substance or mixture of substances which exothermically react in contact with one another.

Communication of heat or cold by a cooling or heating medium is achieved by a connecting conduit or connecting rod 104 integral with the conductive layer, for receiving a hot or cold medium. Connecting conduit 104 can be solid or tubular, and is also preferably flexible, malleable, or capable of being molded into shape by the user. When connecting conduit 104 is a hollow or tubular embodiment, the connecting conduit can further comprise a delivery port 105 at its receiving end, and delivery port 105 can further include a valve 106 for regulating flow of the hot or cold medium to the port, conduit, or conductive material or layer.

Also included in certain embodiments of a system in accordance with the subject invention is a dual-chambered canister providing at least two heating or cooling media from a single source. Preferably, the dual-chamber canister allows the contents to be contained within the chambers under positive pressure, such that the contents readily exit the chambers when the pressure is released.

Figure 2:
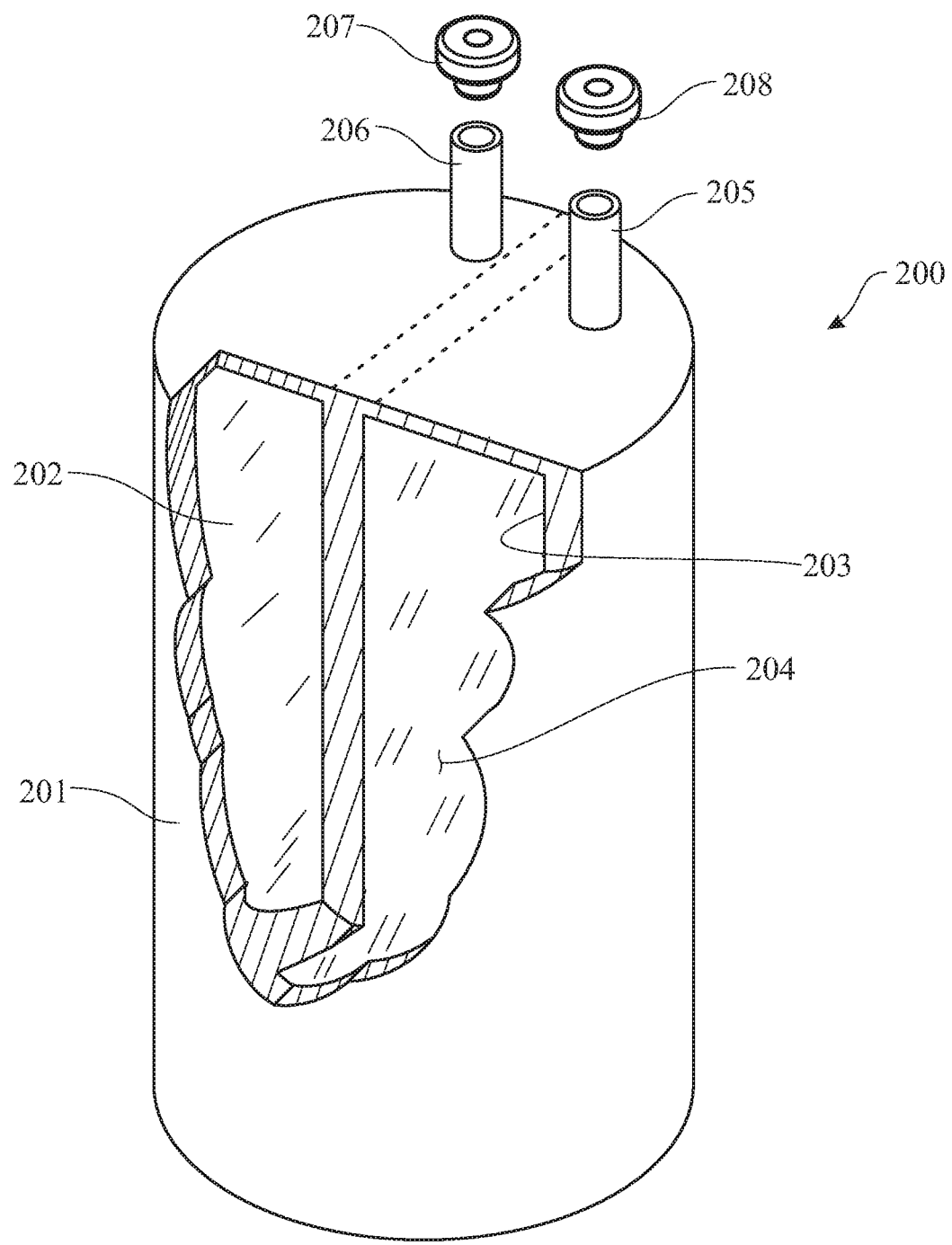
FIG. 2 shows a cutaway view of a dual-chambered canister of the invention.

One embodiment of a dual canister is shown in FIG. 2. The canister 200 comprises an outer containing wall 201 housing a first chamber 202 and a second chamber 203 which are completely separated from one another by a dividing barrier or wall 204 within the canister.

Each chamber can contain different cooling or heating media or each chamber can contain a portion of two media which, when mixed, provide a single heating or cooling medium. In one preferred embodiment, a cooling medium is contained within one of the chambers, e.g., 202, and a heating medium is contained within the other chamber, e.g., 203, or vice versa. This configuration allows a heat source and a cold source form a single canister. Alternatively, the respective chambers can each contain a separate fluid, liquid, solid, or gas which, when mixed together, endothermically or exothermically react with one another to form a cooling or heating medium which can be delivered to the device.

As further shown in FIG. 2, each chamber is independently in communication with the outside of the canister through a nozzle 205 or 206, which allows the contents of the chamber to exit the canister. More preferably, each nozzle 205 and 206 can comprise a valve, 207 or 208 to regulate the flow of the medium from the canister to the outside.

When two or more different media are mixed together to form an endothermic or exothermic reaction, the nozzles 205 and 206 can be connected or communicated to one another by a single mixing tube or conduit which can then engage or be connected to the connecting conduit 104 of the of the pad (see FIG. 1).

Figure 3:
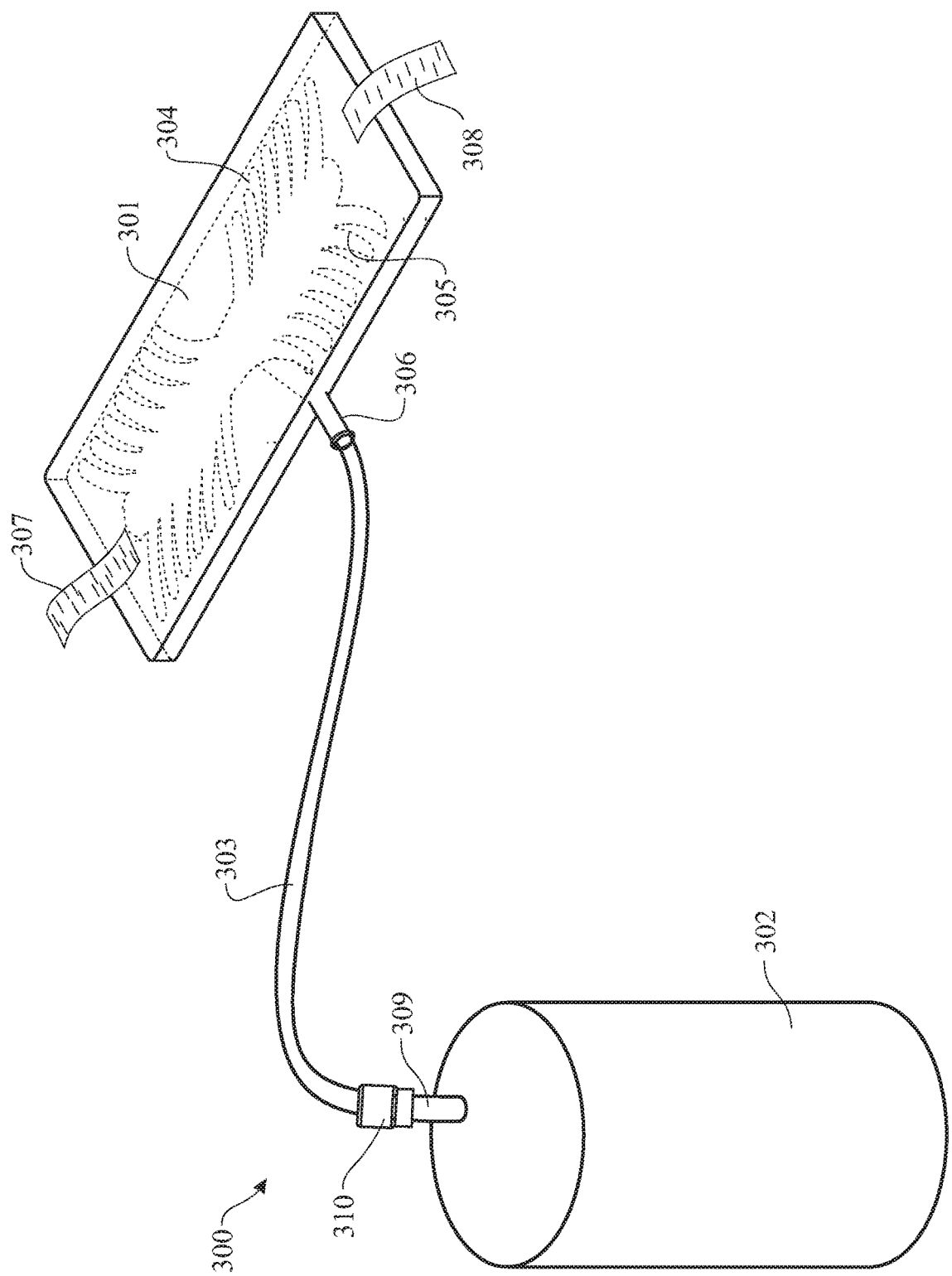
FIG. 3 illustrates an embodiment of the system and components thereof, including the pad, canister of cooling or heating medium source, and delivery conduit.

FIG. 3 illustrates an embodiment of a system according to the subject invention, the system 300 comprising a pad 301, a portable canister 302 housing a heating or cooling medium as a source of heat or cold for the pad, and a delivery conduit 303 in communication with the pad 301 and canister 302 for delivery of heating or cooling medium to the pad from the source. In FIG. 3, pad 301 is further illustrated to comprise straps 307 and 308 for affixing or enwrapping the pad to the body area. A temperature-retentive material 304 within the pad, is shown in broken lines since it is layered within the interior of the pad and is not seen from the outer surface. Also shown in broken lines is the connecting conduit or tube 305 by which cooling or heating media contact the conductive material 304. The connecting conduit 305 comprises a port 306 communicating the connecting conduit 305 with delivery conduit 303.

Delivery conduit 303 is connected at one end to port 306 of the pad 301, and is connected at its other end to the heating or cooling medium source. Delivery conduit 303 is typically connected to the pad and heating or cooling medium source only during the time of cooling or heating the conducting material within the pad and is removed and can be stored during use of the pad. Delivery conduit 303 serves to deliver heating or cooling medium from the source, e.g., canister 302, and connects to the canister nozzle 309.

Alternatively, delivery conduit 303 can communicate with the canister nozzle 309 via a valve 310 connected to the canister nozzle 309.

Figure 4A:
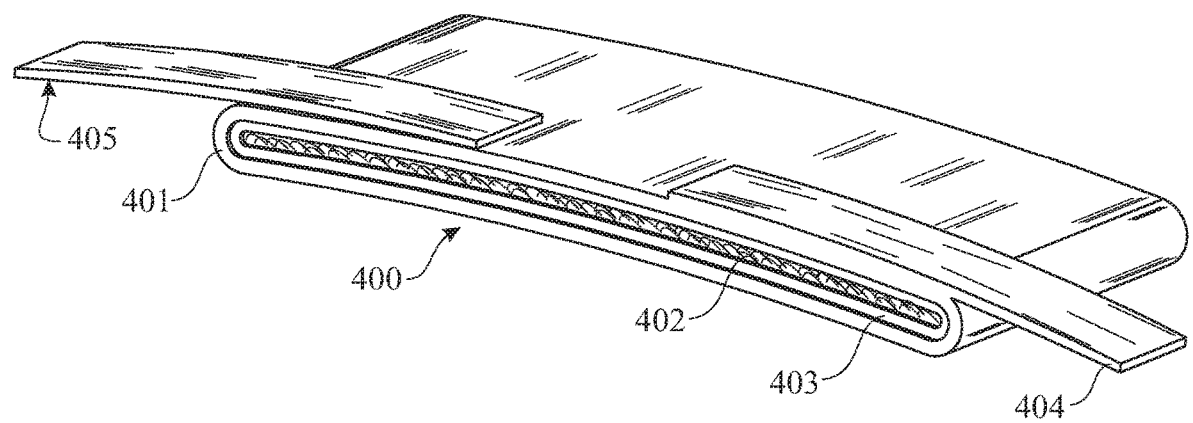
FIG. 4A shows a sectioned view of an alternative embodiment of a pad according to the subject invention wherein the temperature-retentive material is provided within a bladder defining a chamber for containing or having its inner surface at least partially coated with the conductive material.
Figure 4B:
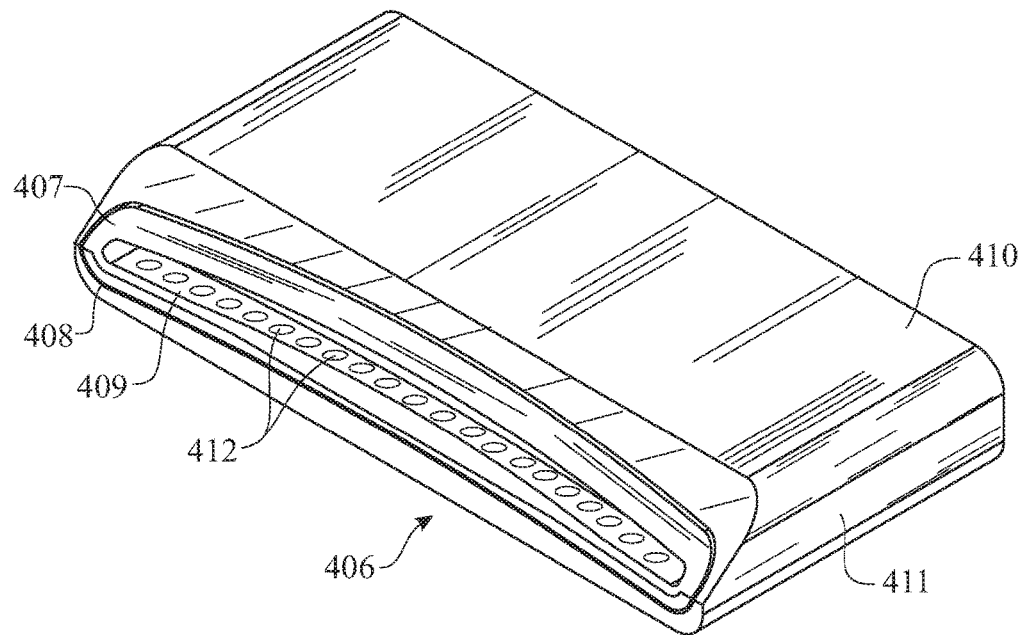
FIG. 4B shows a sectioned view of a pad embodiment comprising the bladder which can further include a gel or other temperature-retentive material in addition to the conductive material or layer on the inner surface of the bladder, and further comprising a protective cover layered over the top face and bottom face of the bladder.

Another embodiment of a pad according to the subject invention, wherein the temperature-retentive material is provided as, or within, a bladder, is shown in FIGS. 4A and 4B. Specifically, FIG. 4A shows a pad 400 comprising a bladder 401 defining a chamber 402 for containing or having its inner surface at least partially coated with temperature-retentive material 403. The temperature-retentive material is shown here not to scale, and is typically a thin layer on the order of 0.1 to 5.0 millimeters in thickness.

The bladder 401 can be formed from any polymeric of textile material, and is preferably a flexible material, capable of being molded or contoured into a shape which fits the contours of the body part when in use. More preferably, the material used to form the bladder can provide the capability for the cold or heat within the bladder to be transferred easily and efficiently to the skin of the user when the pad is in use. The temperature-retentive material within the chamber of the bladder, or coating the inner walls of the bladder can be, for example, aluminum oxide, or other alloy, as would be recognized in the art.

The embodiment of the bladder pad of FIG. 4A is shown further comprising at least one attachment means, and is shown here having an attachment means 404 or 405 comprising two straps 404 and 405 which are affixed to the bladder or a covering thereof, and can encircle a body part and be affixed to one another to secure the pad in place on the body. As would be readily understood, the attachment means can be a single strap, such as an elastic band encircling the pad and allowing to be expandably enwrapping the body part, or can be more than one attachment means, such as one or more straps which can be affixed together by an attachment means such as ties, hooks, buttons, snaps, or hook-and-loop material.

FIG. 4B shows a cooling or heating pad embodiment 406 comprising a bladder 407 defining a chamber 409. The inner surface of the bladder can comprise a layer of temperature-retentive material 408, and can further comprise additional temperature-retentive material 412, which can be gel or other heat or cold-retaining materials formed as beads or particles, or can be an amorphous fluid. The pad 406 can further comprise an outer covering.

Preferably the outer covering is positioned to cover the top face (the outer face, not typically in contact with the skin), the bottom face (inner face, contacting the skin) or both. When covering both faces, the outer cover can be formed as separate pieces adjoined together, or can be a single unitary piece covering at least the top and bottom faces of the bladder.

Generally, the covering serves as a protective layer, for the pad, the skin, or both. Accordingly, the material used is adapted for such use in accordance with its position. For example, a covering for the inner face contacting the skin can preferably be any polymeric or textile which can be comfortable in use, so long as it allows the cold or heat from the pad to transfer to the skin to carry out effective heat or cold therapy.

For the outer layer which is positioned away from the skin surface when in use, a preferred material is an insulating material, e.g., a polymeric material which can prevent, reduce or retard loss of heat or cold from the pad. One preferred embodiment of a material used for an outer covering of a pad is a polymeric foam material, wherein air pockets are present within the material. Air is known as an effective heat or cold insulator and materials comprising air pockets, such as a bubble wrap material, are effective for such purposes.

Yet another embodiment of the invention comprises a chambered pad as illustrated in FIGS. 5-9. The chambered pad embodiment comprises an outer housing, preferably a flexible outer housing, which is preferably a non-porous or polymeric material which bounds at least one chamber having an upper or lower chamber portion. Alternatively, the upper and lower portion of the chamber can be divided or separated by a layer or wall to form at least two discrete chambers, i.e., one or more upper chamber and one or more lower chamber. Although this embodiment can be used for heating or cooling therapy for an area of the body of a person in need thereof, further description of this embodiment refers to cooling therapy and use of a cooling medium or coolant to charge the pad for use as a cooling pad or "cold-pack" therapy.

Preferably, the one or more chambers can expand when the pad is charged with coolant, allowing for expansion of the volume of the cold-retaining or conductive material, as well as permitting excess amount of coolant to be delivered to the chamber of the pad. Excess coolant can be vented from chamber through exit ports or vents. Thus, the outer flexible housing material can be elastic or can comprise one or more pleats or folds to allow for expansion of the chamber volume therewithin.

Figure 5:
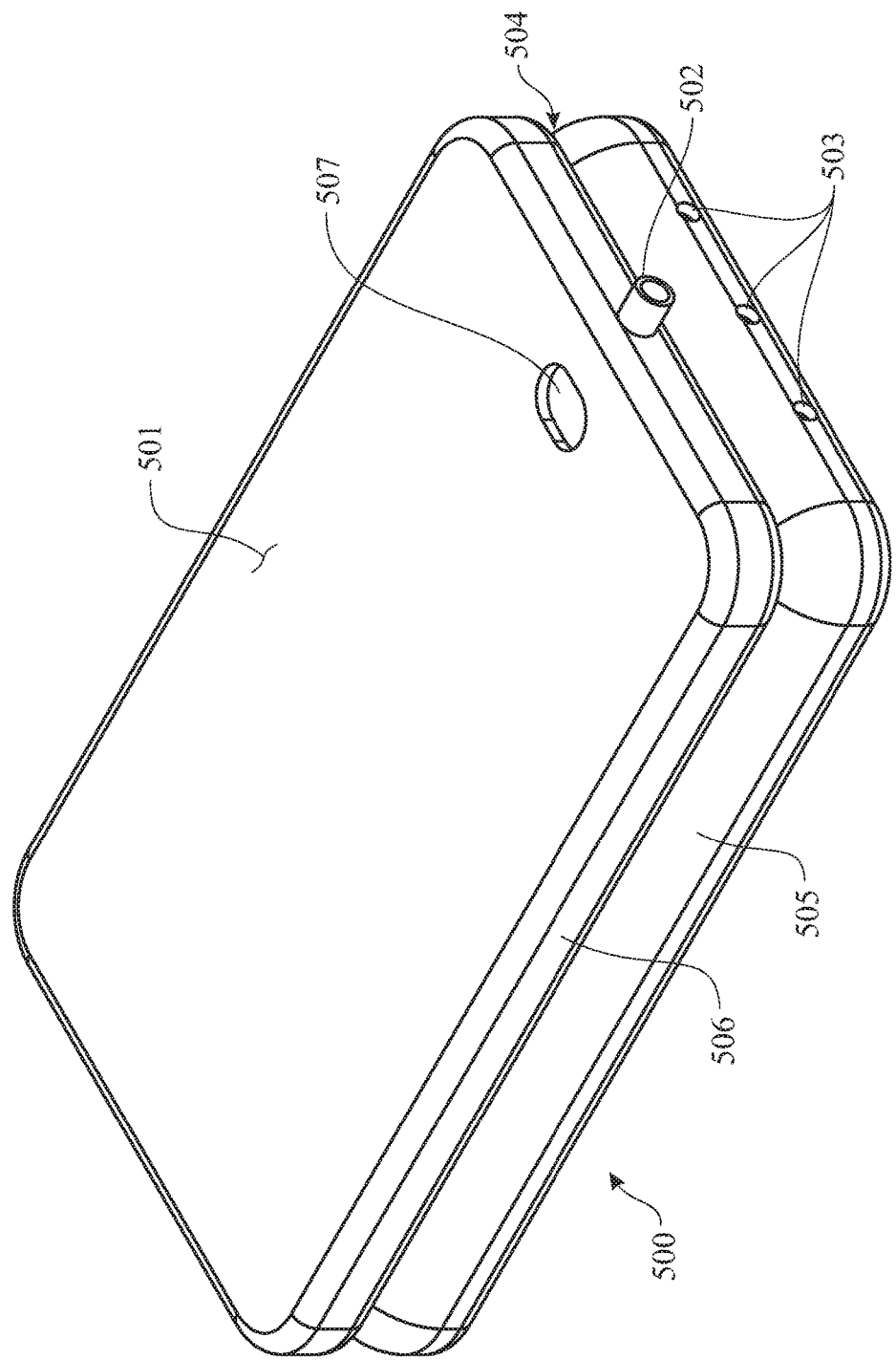
FIG. 5 is a perspective view of an embodiment of a chambered pad according to the subject invention.

As shown in FIG. 5, the chambered pad 500 comprises an outer flexible housing 501 which comprises a delivery port 502 in the upper chamber portion or upper chamber 506 for delivering coolant and charging the pad. The exit ports or vents 503 are shown in communication with the lower chamber portion or lower chamber 505. Also illustrated in FIG. 5 is the fold or pleat area 504 demarcating the upper and lower chambers or chamber portions. Optionally, the cooling pad can include a valve to control the flow of coolant to the pad. The valve (not shown, but conventionally employed in the art) can be operated by an on/off button 507 which toggles the valve open or closed as desired.

Figure 6:
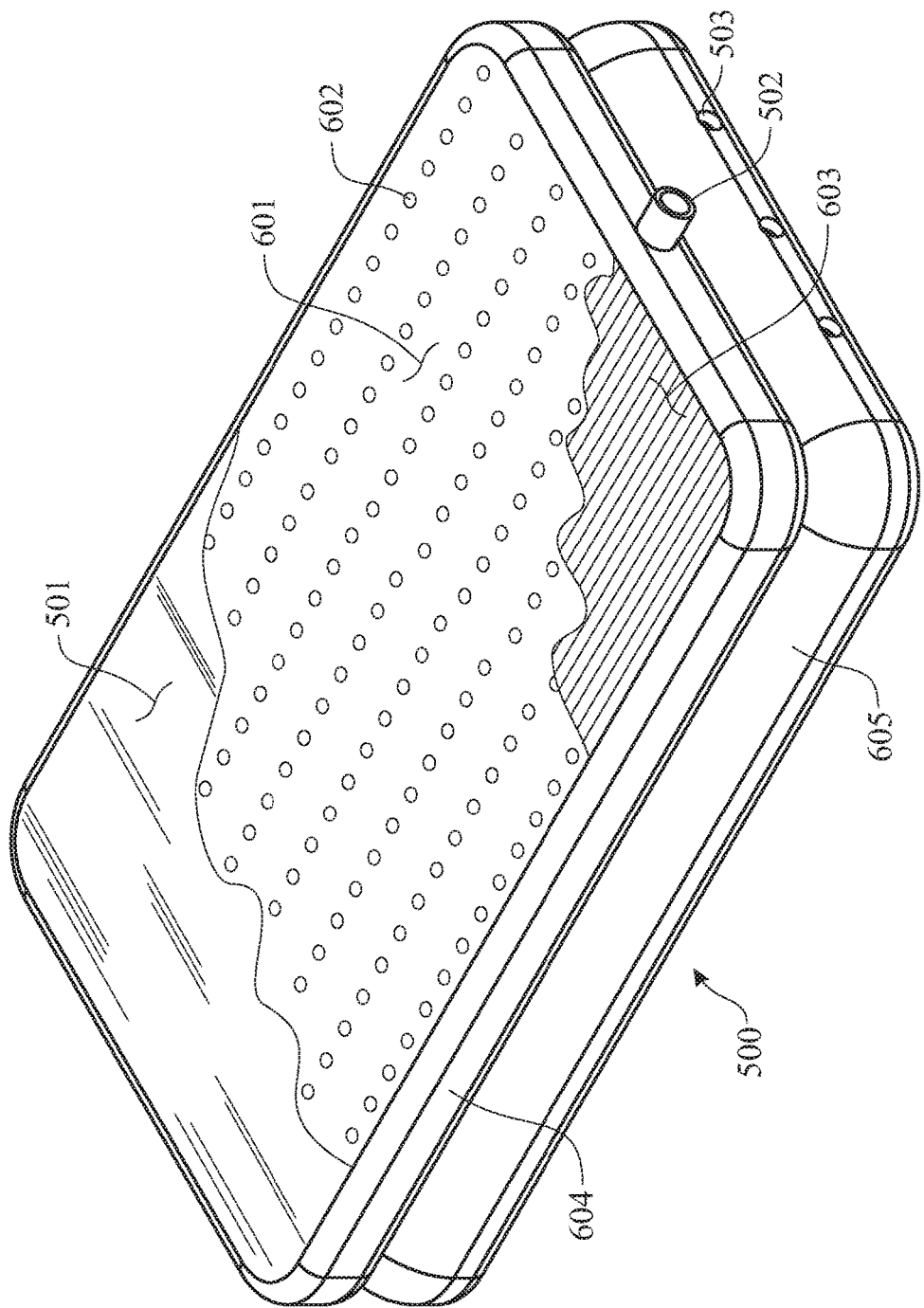
FIG. 6 is a sectioned perspective view of a chambered pad shown in FIG. 5, illustrating the inner chambers, porous separating layer, and temperature-retaining material within the lower chamber.

The chambers or chamber portions of the chambered pad are illustrated in FIG. 6. FIG. 6 shows chambered pad 500 of FIG. 5 in sectioned view, showing the inner chambers formed within the outer flexible housing 501. Within the outer flexible housing 501 is a hollow upper chamber 604 which is bounded by a wall or floor or separating layer 601. Here, separating layer 601 is shown comprising a plurality of pores 602 which permit coolant delivered into the upper chamber 604 to pass through the pores and into the lower chamber 605. Positioned below separating layer 601 and within lower chamber 605 is a cold-retaining or conducting material 603, such as a polymeric gel.

The chambered pad of FIG. 6 also shows, as in FIG. 5, the delivery port 502 in communication with upper chamber 604, and exit ports or vents 503 in communication with lower chamber 605.

Figure 7:
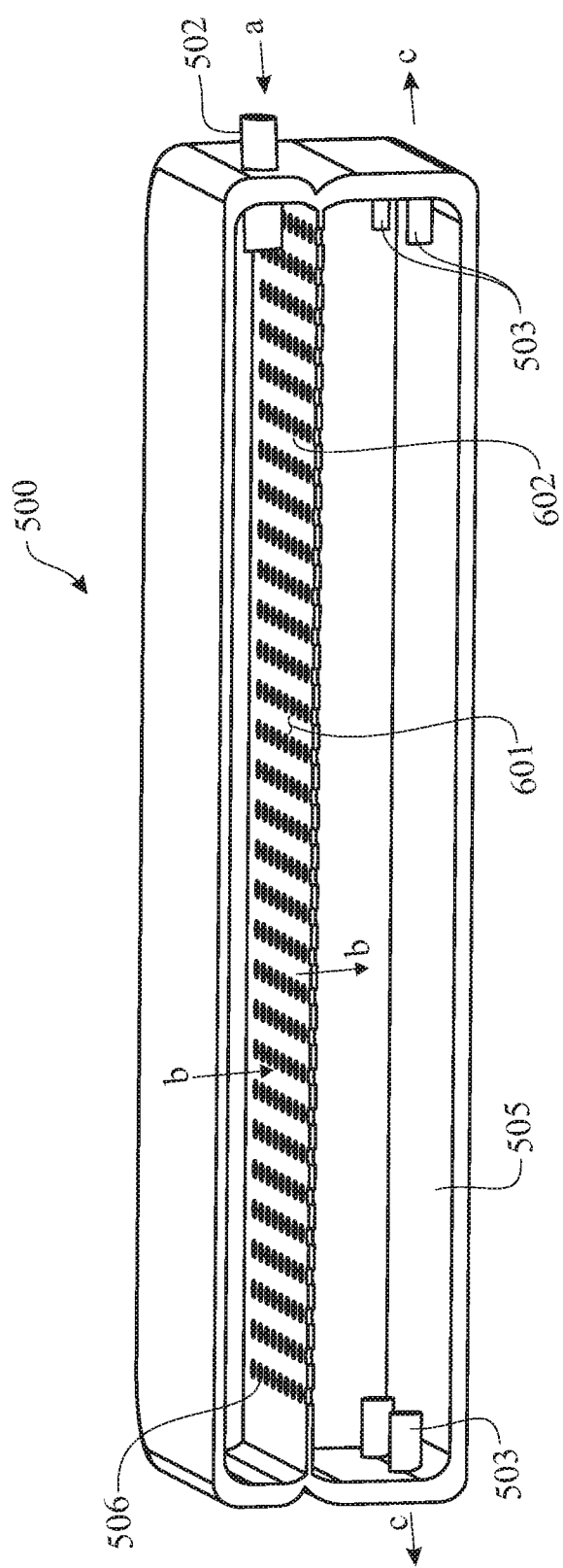
FIG. 7 is a cross-section view of a chambered pad shown in FIG. 5, illustrating the flow of cooling or heating medium into the upper chamber through the delivery port, from the upper chamber through the porous separating layer to the lower chamber, and out the exit port or vents.

FIG. 7 shows an embodiment of chambered pad 500 in a side, cross-sectioned view to illustrate the flow of coolant when delivered to the pad. Coolant is delivered through delivery port 502 in the direction of arrow a, into the upper chamber or upper chamber portion 506. Coolant then passes from upper chamber or chamber portion 506 into lower chamber or chamber portion 505, in the direction of arrows b, through separating layer 601 via pores 602 formed therein. Excess coolant can then exit or escape from lower chamber or chamber portion 505 through exit ports or vents 503 in the direction of arrows c into the environment.

Figure 8:
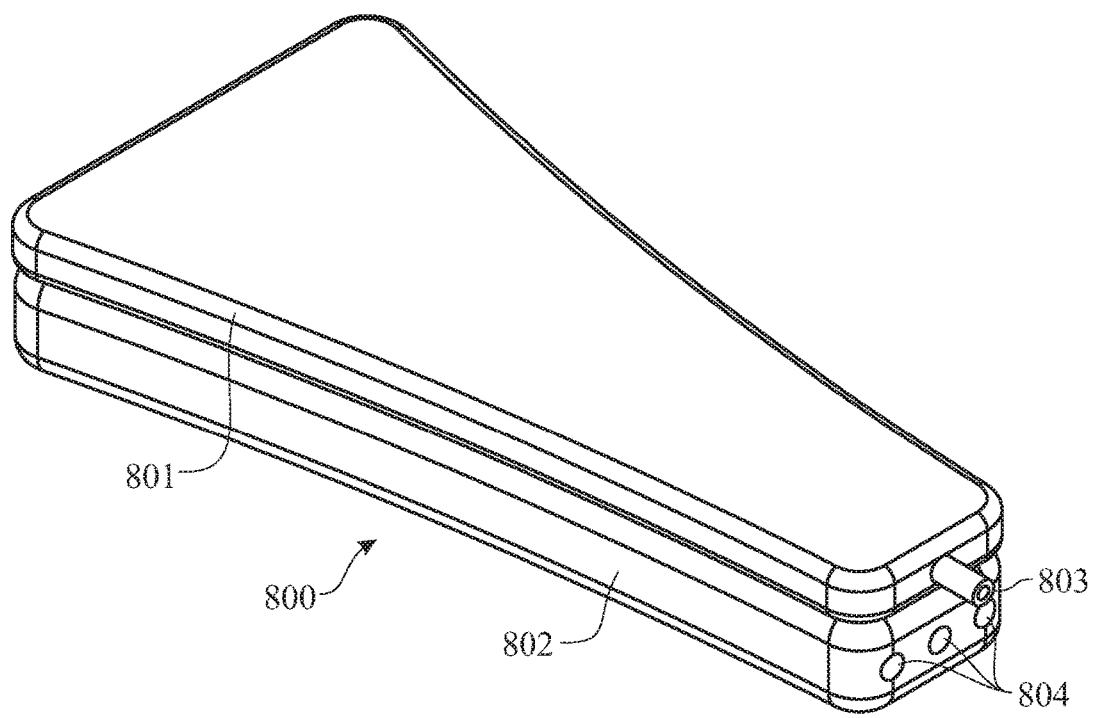
FIG. 8 is a perspective view of a chambered pad embodiment of the subject invention, configured as an elongated shaped pad preferable for positioning between the legs of a subject.

Alternative shapes and configurations of a chambered pad according to the subject invention can be manifold and would be readily understood and recognized by a person of ordinary skill in the art to be available according to the need of positioning on the body. For example, an elongate-shaped configuration for a pad of the invention is illustrated in FIG. 8. The elongate pad 800 includes upper chamber or chamber portion 801 and lower chamber or chamber portion 802. A delivery port 803 is shown in communication with upper chamber or chamber portion 801 and exit ports or vents 804 are shown in communication with lower chamber or chamber portion 802.

The elongate-shaped embodiment of the chambered pad can advantageously be positioned in areas of the body in need of an elongated cooling pad. For example, an elongated cooling pad can be advantageously positioned between the legs of a subject, such as in the groin area following hernia surgery or on a male following vasectomy or prostate surgery.

Figure 9:
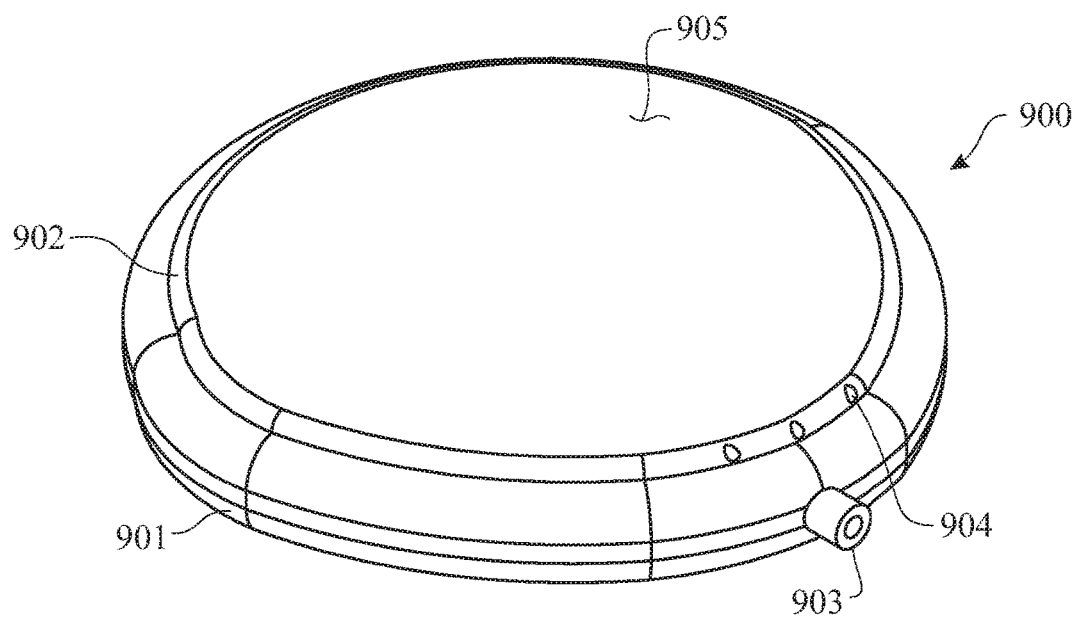
FIG. 9 is a perspective view of a chambered pad embodiment of the subject invention configured as a rounded shaped pad preferable for rounded areas of the body, e.g., breast area.

Another embodiment of a chambered pad of the invention comprises a round- or cup-shaped configuration, as illustrated in FIG. 9. Round- or cup-shaped pad 900 is shown illustrating the inner surface 905 which contacts the body when in use. Accordingly, FIG. 9 shows upper chamber or chamber portion 901 below lower chamber or chamber portion 902. Delivery port 903 is shown in communication with upper chamber or chamber portion 901 and exit ports or vents 904 are shown in communication with lower chamber or chamber portion 902.

The rounded pad configuration 900 shown in FIG. 9 can be advantageously positioned on rounded areas of the body in need of a round- or cup-shaped cooling pad for improving contact with rounded areas of the body. For example, a round- or cup-shaped cooling pad can be advantageously positioned in contact with the breast of a female subject for cold therapy following breast augmentation surgery.

FIGS. 10A-10G illustrate various views of a further embodiment of a cooling or heating pad of the subject invention wherein a temperature-retentive material is disposed within a single chamber bounded by a cover or housing. Preferably, the temperature-retentive material is provided as an enwrapped or encased temperature-retentive packet. In this embodiment, the conduit for delivery of the cooling or heating medium extends through an entry port formed in the housing or cover and into the chamber, such that the conduit extends over at least a portion of the temperature-retentive material or packet. The distal portion (distal to the heating or cooling medium source) of the conduit can be linear or straight, or can be branched within the chamber. The distal portion (or portions, if branched) of the conduit comprises one or more exit ports so that cooling or heating medium delivered via the conduit exits the conduit and is dispersed onto, or in close proximity to, the temperature-retentive material or packet.

Figure 10A:
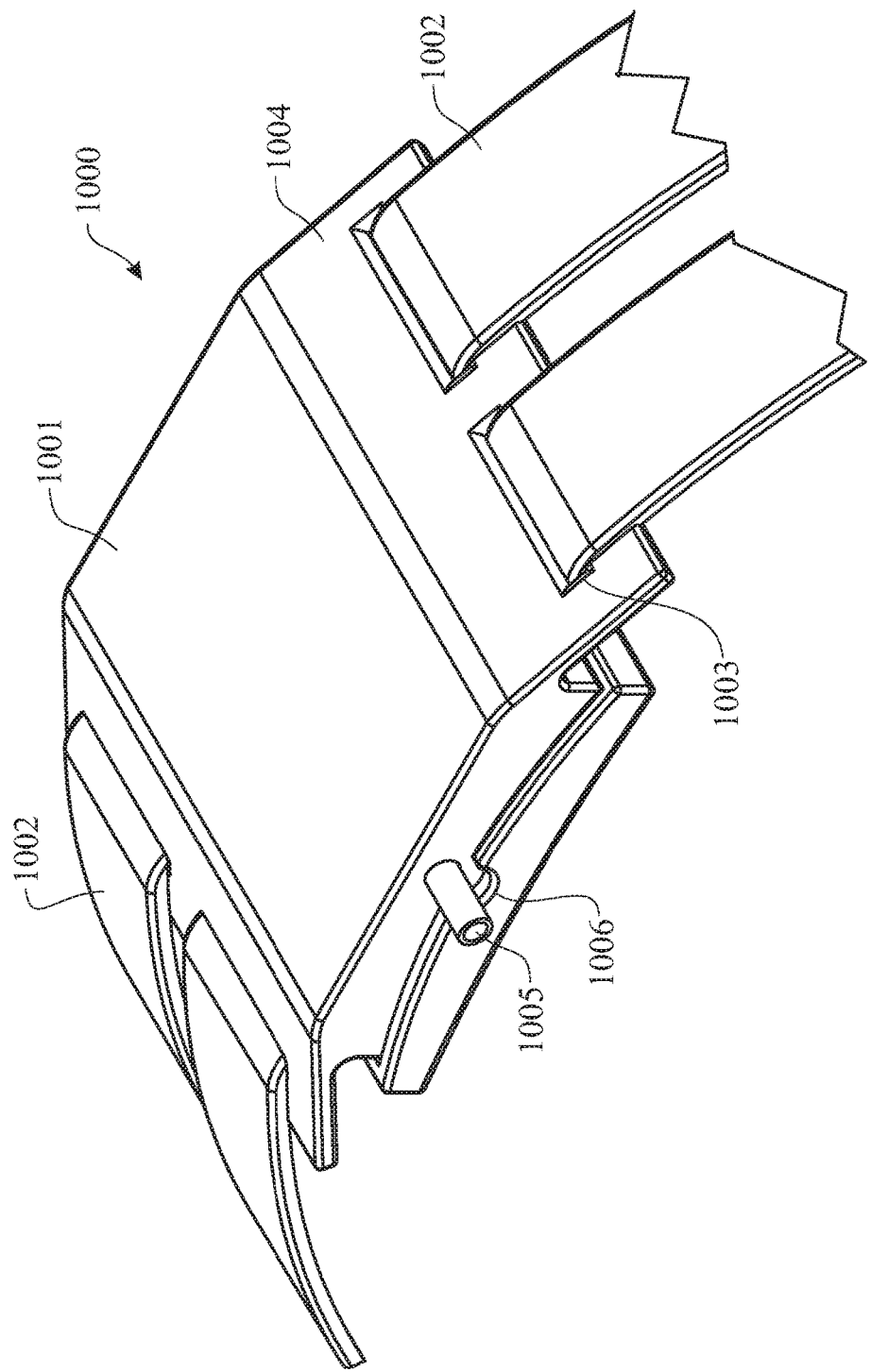
FIG. 10A is a top, perspective view of a pad embodiment in accordance with the subject invention.

FIG. 10A shows a perspective view of a cooling or heating pad 1000 comprising an outer housing or cover 1001, bounding a chamber therewithin. Integral with the housing or cover are attachment means, e.g., bands or straps 1002 for affixing the pad in a desired position on the body. In this embodiment, the bands or straps 1002 are attached to the housing or cover 1001 by means of slots 1003 formed in a cover flange or wing 1004 which can be integral with the cover or housing, said flange or wing being formed as part of or separately from the housing or cover. The band or strap attachment means is not intended to be limiting in any way, as band or strap configurations for affixing a cooling or heating pad are well known in the art, any of which may be adapted for use with the subject invention. For example, FIG. 10A depicts a pair of bands or straps on each side of the pad. Clearly, a single band or strap or a plurality, e.g., four or more, straps can be used. These bands or straps can affix to the pad housing or cover, or can be affixed to one another by means of a buckle, snap, hook-and-loop material, or the like, or may be unified as an elastic wrist band, similar to sweat band used on wrists in athletics.

FIG. 10A further illustrates the conduit 1005 for delivering heating or cooling medium to the pad. Conduit 1005 is shown to extend into the chamber formed by the housing or cover 1001, which is accessed via an entry port 1006 provided in the housing or cover.

Figure 10B:
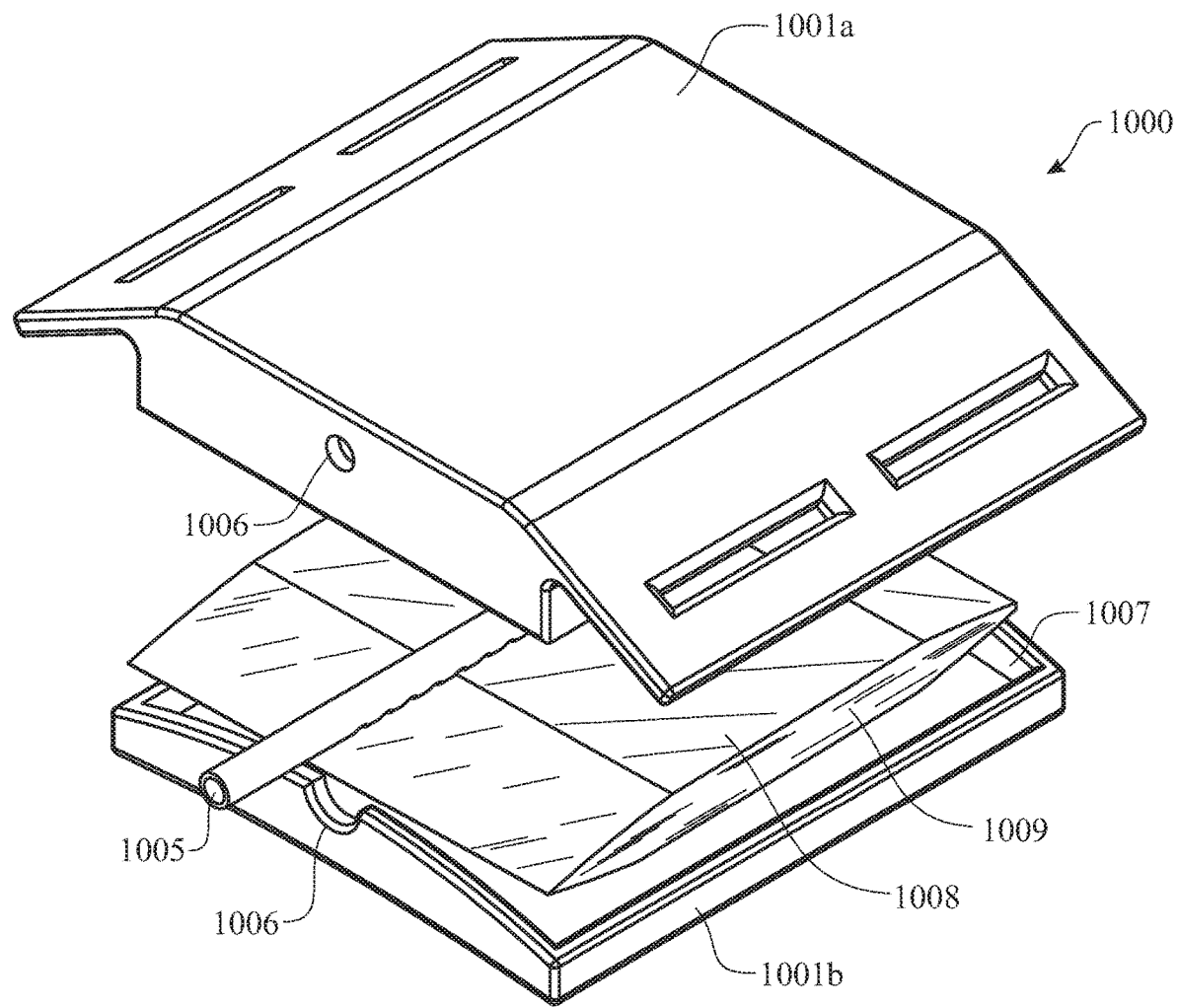
FIG. 10B is an exploded top perspective view of a pad embodiment in accordance with the subject invention.

Extension of the conduit into the chamber formed within the housing or cover is illustrated in FIG. 10B, which is an exploded perspective view of the pad 1001 shown in FIG. 10A. Specifically shown is conduit 1005 extending into chamber 1007 formed between an upper portion of the housing or cover 1001a and a lower portion of the housing or cover 1001b, through entry port 1006. The upper and lower portions of the housing or cover are shown to be separate or discrete sections which can engage one another to form a housing or cover unit. However, it would be understood that the two separate sections can be molded or otherwise formed together, as a single unit, so long as a chamber is provided therein, and an entry port is provided to allow for the conduit to extend into the chamber from outside the housing or cover.

FIG. 10B further shows a temperature-retentive material 1008 disposed within the chamber. Here, the temperature-retentive material is shown as a temperature-retentive packet 1009, which comprises a temperature-retentive material enwrapped or encased within a layer or membrane of material to provide a unitary and disposable package of temperature-retentive material. Further illustrated in FIG. 10B is the flange or flanged edging 1009 around the periphery of the packet 1008, which can be useful for disposing the temperature retentive packet within the chamber in a stationary manner. As described herein, the flange or flanged edge can be affixed to a holding peg, can be held by means of a flexible retaining ring, such as an O-ring, engaging a ridge or groove formed in the outer perimeter of the housing, or can be grasped and held or "pinched" between the tightly engaged edges of the upper and lower portions of the housing or cover.

Figure 10C:
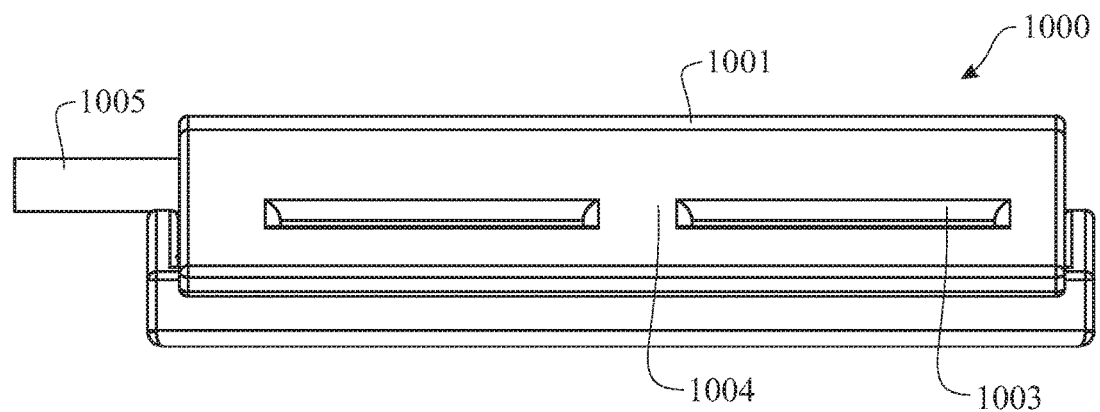
FIG. 10C is a side plan view of a pad embodiment in accordance with the subject invention.

The pad embodiment of FIG. 10A is shown in side plan view in FIG. 10C, depicting the pad 1000 comprising a housing or cover 1001, flange or wing 1004 having one or more slots 1003 for engaging a band or strap (not shown), and a cooling or heating medium conduit 1005 for delivering heating or cooling medium to the inner portion of the housing or cover, i.e., the chamber, of the pad.

Figure 10D:
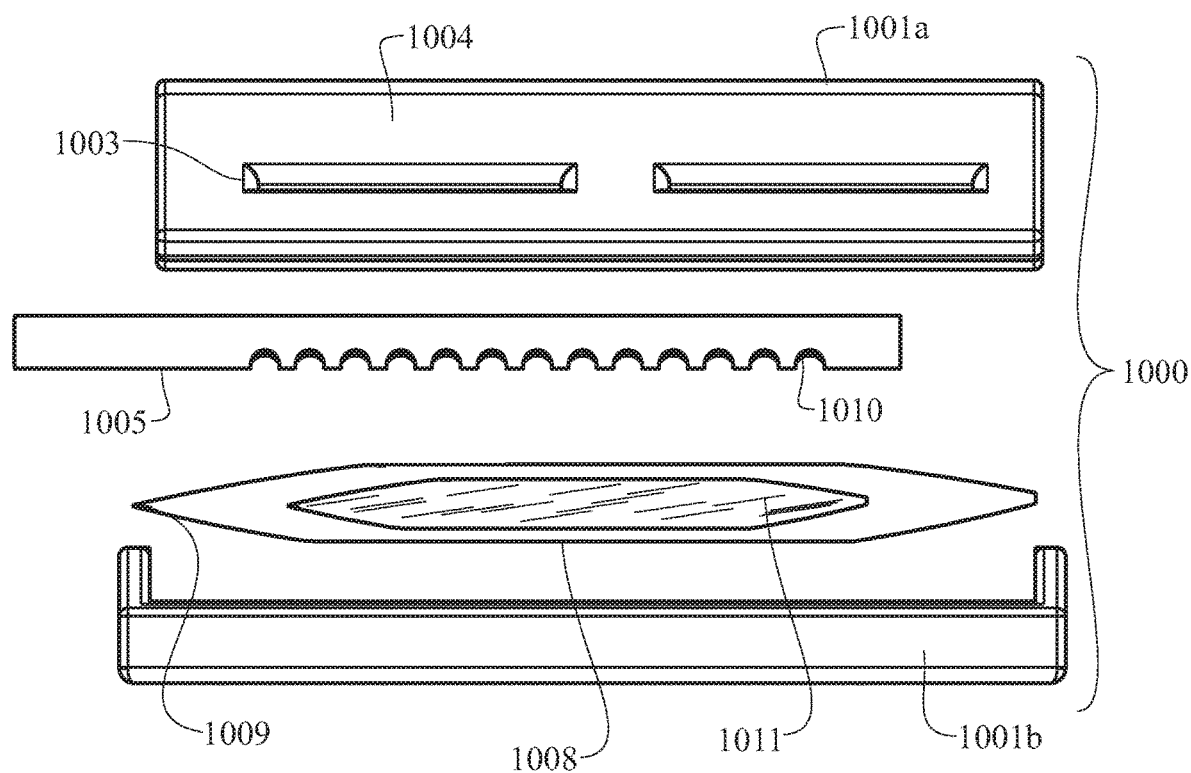
FIG. 10D is an exploded side plan view of a pad embodiment in accordance with the subject invention.

This side view of pad 1000 is shown in exploded side view in FIG. 10D. This view provides illustration of an upper housing or cover portion 1001a and lower cover or housing portion 1001b. The upper and lower housing or cover portions can engage with one another to form a single cover or housing (1001 in FIGS. 10A, 10B, and 10C) having a chamber formed within said housing or cover. Upper housing or cover portion 1001a further comprises one or more flange or wing 1004 having at least one slot 1003 firmed therein for receiving and affixing a band or strap (not shown) thereto. Within the chamber formed within the housing or cover, temperature-retentive material 1011 can be disposed. In this illustration, the temperature-retentive material is provided as a temperature-retentive packet 1008, which comprises temperature-retentive material enwrapped or encased in a layer or membrane.

The layer or membrane enwrapping or encasing the temperature-retentive material can extend from the edges thereof to form a flange or flange edging 1009. This flange or flanged edging of the temperature-retentive packet can advantageously provide for securing the temperature-retentive packet in position within the chamber. For example, the flange or flanged edging of the temperature-retentive packet can be secured using a peg or snap engagement means, by a retaining ring, e.g., an O-ring, engaging a ridge or groove formed in the housing or cover, or can be secured between the upper and lower portions of the cover or housing when engaged together to form a single housing or cover unit.

Further illustrated in HG. 10D is conduit 1005 for delivering cooling or heating medium to the pad, and specifically, to the temperature-retentive material. As shown, one end of the conduit (the "proximate" end, referring to the end more proximate to the source of the heating or cooling medium) is outside the housing or cover, and the other end of the conduit (the "distal" end, referring to the end more distal to the source of heating or cooling medium) extends within the housing or cover. In addition, conduit 1005 comprises one or more openings, apertures, pores, or ports 1010 which allow for heating or cooling medium to exit via the conduit and be dispersed over the temperature-retentive material or temperature-retentive packet, thereby activating or "charging" the temperature-retentive material or packet with cold or heat as desired.

Figure 10E:
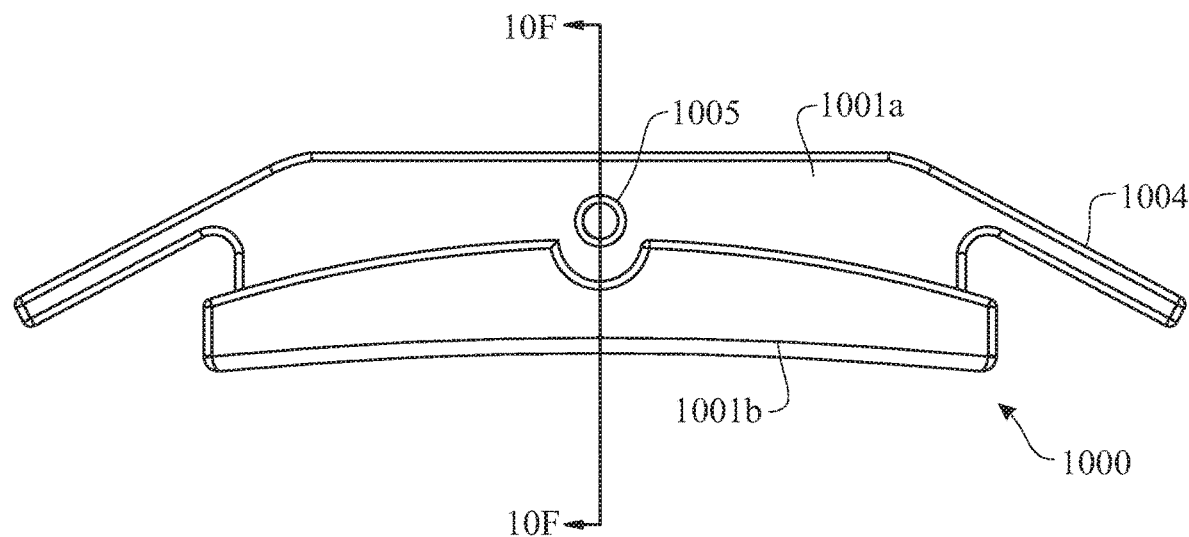
FIG. 10E is a front plan view of a pad embodiment in accordance with the subject invention.

FIG. 10E is a front plan view of a pad 1000 of the subject invention comprising upper housing or cover portion 1001a, including a flange or wing 1004 as described, lower housing or cover portion 1001b which can include an insulating or protective layer or can permit space to bound an insulating or protective layer provided on a skin-contacting face of the temperature-retentive material or packet, and conduit 1005. This view provides line A-A, along which the cross-sectional view in FIG. 10E is shown.

Figure 10F:
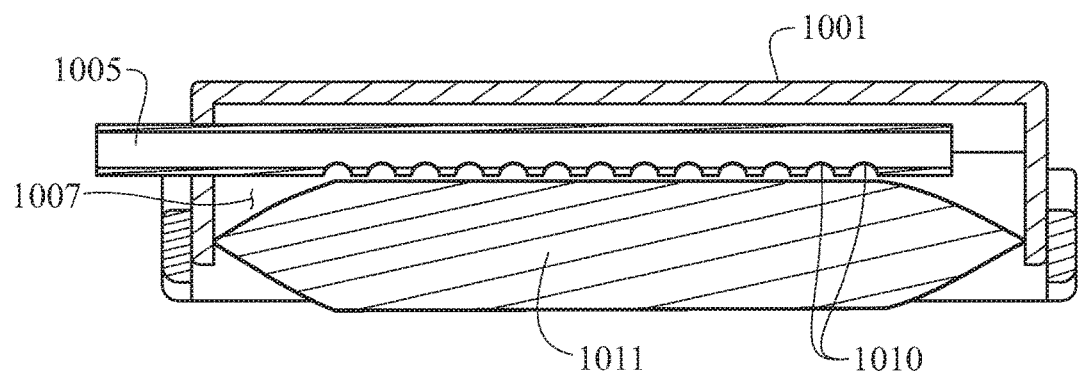
FIG. 10F is a cross-sectional side plan view of a pad embodiment in accordance with the subject invention.

Specifically, as provided in FIG. 10F, cross-sectional front plan view illustrates housing or cover 1001 forming a chamber 1007 therewithin, containing distal portion of conduit 1005. The distal portion of conduit 1005 includes exit ports 1010, which deliver and disperse heating or cooling medium to temperature-retentive material 1011 also disposed with chamber 1007 of the pad.

Figure 10G:
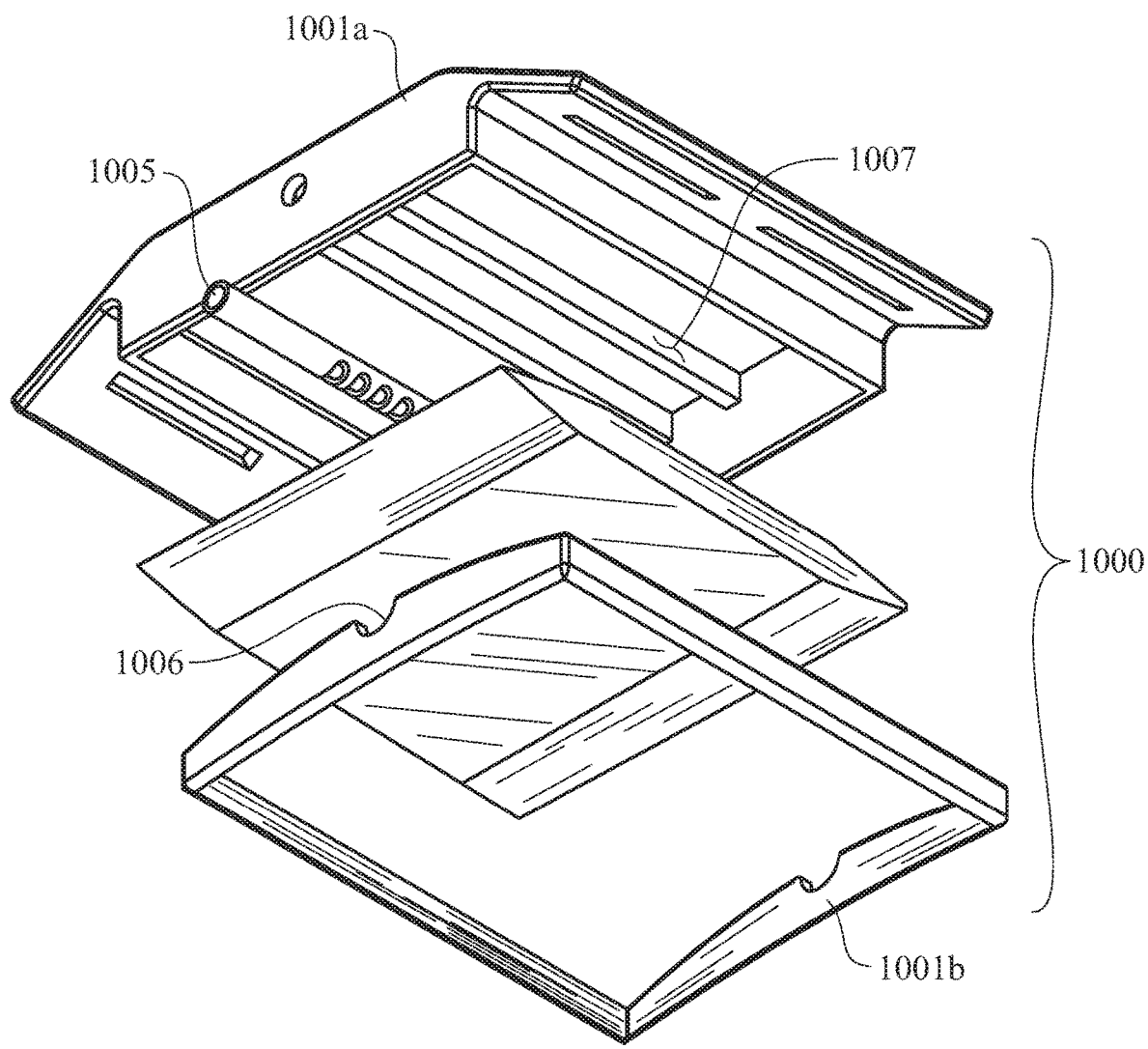
FIG. 10G is an exploded bottom perspective view of a pad embodiment in accordance with the subject invention.

FIG. 10G is an exploded bottom perspective view of pad 1000, illustrating upper housing or cover portion 1001a and lower housing or cover portion 1001b, which provide chamber 1007 therewithin, and receiving conduit 1005 through an entry port 1006. In this view, bottom housing or cover portion 1001b is shown having a curved or body-contouring shape.

The embodiments described for the subject system, pad, and method have numerous uses and applications, including for post-surgical treatment of an area of the body, reduction of fever or hyper- or hypothermia conditions, for minimizing bruising, for emergency application in minimizing tissue damage following a heart attack, for fertility purposes (such as maintaining coolness in the groin or scrotal area). The device can advantageously be shaped to conform to a particular area of the body, and can be gender-specific, such as being shaped for women following breast augmentation procedures, or for men following vasectomy or hernia repair procedures.

The malleability or molding capability of the pad to conform to a specific area of the body is facilitated by the portability of the pad. Specifically, the pad can be placed at the site to contact the body in a form-fitting manner, then frozen in situ using the cold or heat medium. This is advantageous over conventional freezer packs which are only generally contoured to an area of the body by being frozen in that general contour shape in a freezer, then removed to be placed onto the area of the body.

In addition, the subject invention contemplates incorporating the device into, or as part of, articles of clothing, including underwear or outer apparel. Outer apparel can include sports uniforms or protective gear, or military uniforms.

The system of the invention, or components thereof, may be used by military personnel who may be injured in line of duty. It provides quick and effective chilling temperature for the affected area. In some instances, it may directly or indirectly allow freezing of the wounded body part to avoid profuse bleeding. The innovative function of this system is utilization of cold or hot temperature created or already in existence by means of liquid, gas, endothermic/exothermic chemicals, in the highly insulated canisters secured by highly conductive inner surface of the container or canister of any size.

Another advantage of the subject invention is that the device can receive either of a heating or cooling medium, such that the therapies can be interchanged, alternating heat or cold for both therapies to the same area of the body, without changing the device.

All embodiments of the single or dual chambered canisters can be refillable with the desired substance or substances. This allows for use of stand-alone or portable sources of cold and/or freezing (or heating) agent(s) with utmost comfort and convenience. The special design and contour of the device that comes in contact with the desired body part contains no bulky wrappings around the affected area and allows the person to wear normal clothing and conduct normal activities while the therapy is at work. It further does not require unwrapping and removal or replacement of the device during intermittent, periodic or continued use.

In preferred embodiments of the invention, the exterior surfaces can be insulated or comprise insulating material to avoid or reduce the time for dissipation of the temperature delivered to the conductive material or layer, thus providing extended use of the device without "re-charging" the temperature.

Other advantages and aspects of the invention include, but are not limited to, the following:

A) Outer layer—Not limited to a particular material or shape and can include a moldable gel material contained in a plastic housing fused or attached to the highly conductive surface whereby gel absorb and maintain the cold (or heat) from the conductive material and transmittable to the outer surface of the pad which can be applied to or placed in contact with the desired body surface. In some embodiments the conductive layer may be covered with a very fine and soft material not limited to conductive textiles readily available, or may be applied directly to the affected area.

B) Conductive Material or Layer—This layer consist of super conductive materials readily available and not limited to flexible or solid materials such as graphene or other materials currently used in geothermal technologies. Materials such as graphene can readily receive and transfer the cold (or the heat) with minimum loss from the source. This layer can be provided as different textures, sizes, or shapes according to the desired design, as would be recognized by persons of ordinary skill in the art. The conductive layer can also include a gel, liquid, solid or plasma. In addition, the conductive layer can further comprise an insulating material layered thereon, such as an insulating or reflective film or ceramic paint, or the like.

C) Outer Surface Material for Pad—The outer surface material used for the pad is not limited to plastic or any type of textile and preferably is an efficient conductor of heat or cold from the conductive material to the outer surface of the pad. The outer layer may be of porous or non-porous material that will allow dissemination of the cooling/heat producing gas or liquid without affecting the properties or allowing leakage of the content. In other embodiment of the invention, a connecting or fastening means, such as a strap, hook-and-loop fastening material, buckle, snaps, or other conventional fasteners, can be formed or provided integral with the cover material so that the device can be wrapped around a body part, such as a leg, arm, neck, or the like. An embodiment comprising a strap fastening means is illustrated in FIG. 3.

D) Delivery conduit—The delivery conduit can be provided in a variety of lengths as desired and serves to connect the cooling (or heating) material from its source to the conductive layer. The delivery conduit can be any shape (e.g., tubal or rectangular) and may be hollow or solid. One embodiment of the delivery conduit comprises a double tubing to allow faster circulation of the cooling or heating medium to all areas of the pad. The delivery conduit can comprise a highly conductive material or can be insulated using, for example, foam, Styrofoam or ceramic paint. Preferably, the delivery conduit comprises a fastening mechanism to engage with a port or nozzle of the cold/hot source. In other embodiments, the connective layer may be fused to the conductive layer.

E) The Cooling/Heating Source—The system comprising a cooling or heating source comprises, preferably a highly insulated container, such as a canister, that can hold a pressurized cooling or heating medium. A preferred cooling medium is liquid nitrogen, but can be carbon dioxide, alcohol, Argon gas, Freon gas, dry ice, refrigerant gas r-134a and or any other cooling substance(s) that may be in liquid, solid or gas form. Release of pressure on the container can cause the medium to exit the container, be carried through the delivery conduit to the connecting conduit and conductive material, whereby the pad surface is heated or cooled for use. In other embodiments, the container may hold highly active endothermic chemicals (or Exothermic to create heat) and may contain conductive gels. Upon excitement of the chemicals cold and freezing temperatures (or heat) will be generated. The container may also include a highly conductive rod that may be hollow or solid of any shape that is located in center of the container and will absorb and retains the cold (or heat). The current will then be transferred to the conductive layer of the pad by engaging it to conductive layer.

Alternatively, the source of cooling or heating can be provided by use of direct or indirect electrical or electromagnetic current, such as battery operated instrument to activate the conductive material within the pad.

It would be understood that the above description is representative of the and fully details the invention and its use. Other or additional embodiments would be recognized as within the scope, and are intended to be part of and included as part of the invention, without departing from the spirit of the invention.

The invention claimed is:

1. A portable heating or cooling pad system for applying hot or cold temperature to an area of a body in need of treatment using hot or cold temperature, said system consisting of:

a) a pad comprising a housing having an upper housing portion and a lower housing portion forming a chamber bounding a temperature-conductive or temperature-retentive gel packet, wherein the upper housing portion is an outer cover having an entry port for receiving heating or cooling medium, and a receiving conduit having a distal portion extending within the chamber and a proximal portion extending through the entry port, the receiving conduit further comprising a plurality of exit ports on its distal portion and positioned proximate to the temperature-conductive or temperature-retentive gel packet allowing for delivery and dispersal of the heating or cooling medium to the temperature-conductive or temperature-retentive gel packet and wherein the lower housing portion is configured to expose a skin-contacting face of the temperature-conductive or temperature-retentive gel packet for contacting the skin of the user;

b) a portable source of cooling or heating medium within a container, said cooling or heating medium being deliverable, as desired, to the connecting conduit and temperature-conductive or temperature-retentive gel packet by c) a detachable delivery conduit for delivering the heating or cooling medium from the portable source to the receiving conduit of the pad and thereby the temperature-conductive or temperature-retentive gel packet within the pad to cool or heat the temperature-conductive or temperature-retentive gel packet and pad for use;

wherein the temperature-conductive or temperature-retentive gel packet is cooled or heated at the applied area of the body without requiring removal of the pad or without requiring continuous circulation of the medium from the source to the pad during use.

2. The system of claim 1 wherein the source of cooling or heating medium is a canister capable of holding the cooling or heating medium under pressure within a canister chamber, said canister comprising a nozzle in communication with the canister chamber, allowing delivery of the medium to the temperature-conductive or temperature-retentive gel packet.

3. The system of claim 1 wherein the medium is a cooling medium comprising liquid nitrogen.

4. A heating or cooling pad for applying hot or cold temperature to an area of a body in need of treatment or therapy using hot or cold temperature, said pad comprising a housing having an upper housing portion and a lower housing, wherein the upper housing portion and lower housing portion form a chamber bounding a temperature-conductive or temperature-retentive gel packet, wherein the lower housing portion is configured to expose a skin-contacting face of the temperature-conductive or temperature-retentive gel packet for contacting the skin of the user and the upper housing portion is an outer cover having an entry port, and a receiving conduit having a distal portion extending within the chamber and a proximal portion extending through the entry port, the receiving conduit further comprising a plurality of exit ports on its distal portion and positioned proximate to the temperature-conductive or temperature-retentive gel packet allowing for delivery and dispersal of a heating or cooling medium to the temperature-conductive or temperature-retentive gel packet while the pad is in use on the body so that the temperature-conductive or temperature-retentive gel packet is cooled or heated at the applied area of the body without requiring removal of the pad or without requiring continuous circulation of the medium from the source to the pad during use.

5. The heating or cooling pad of claim 4 further comprising an attachment means selected from the group consisting of a strap, buckle, snaps, or hook and loop material, wherein the attachment means facilitates positioning the pad in a fixed position in relation to the area of the body.

6. A method of providing heat or cold therapy to an area of a body, said method comprising:

a) providing a pad of claim 4;

b) applying the pad to the area of the body in need of heat or cold therapy; and c) cooling or heating the temperature-conductive or temperature-retentive gel packet using a cooling or heating medium delivered to the pad from an external source by a detachable delivery conduit connecting the external source and the pad to cool or heat the temperature-conductive or temperature-retentive gel packet and thereby cool or heat the pad and the area of the body in need of heat or cold therapy.

7. The method of claim 6 wherein the temperature-conductive or temperature-retentive gel packet is cooled using liquid nitrogen.

8. The method of claim 6 wherein the method comprises alternating heat and cold therapy by using the pad without removing the pad between heat and cold therapies.

* * * * *